United States Patent
Bojovic et al.

(10) Patent No.: US 7,266,408 B2
(45) Date of Patent: Sep. 4, 2007

(54) DEVICE AND PROCEDURE FOR VISUAL THREE-DIMENSIONAL PRESENTATION OF ECG DATA

(75) Inventors: Bosko Bojovic, Belgrade (YU); Ljupco Hadzievski, Belgrade (YU); Petar Belicev, Belgrade (YU)

(73) Assignee: NewCardio, Inc., San Jose, CA (US)

( * ) Notice: Subject to any disclaimer, the term of this patent is extended or adjusted under 35 U.S.C. 154(b) by 259 days.

(21) Appl. No.: 11/036,930

(22) Filed: Jan. 14, 2005

(65) Prior Publication Data

US 2005/0209525 A1 Sep. 22, 2005

(30) Foreign Application Priority Data

Jan. 16, 2004 (YU) .................................. 0043/04

(51) Int. Cl.
*A61N 5/0402* (2006.01)

(52) U.S. Cl. .................................................. 600/512

(58) Field of Classification Search ............... 600/512
See application file for complete search history.

(56) References Cited

U.S. PATENT DOCUMENTS 5,803,084 A * 9/1998 Olson ......................... 600/512
6,128,526 A   10/2000 Stadler et al.
6,804,550 B1 * 10/2004 Murray ........................ 600/509

FOREIGN PATENT DOCUMENTS

WO   WO-00/14687 A1   3/2000
WO   WO-03/057031 A1  7/2003

OTHER PUBLICATIONS

Antman, E.M. et al. (2004). "ACC/AHA Guidelines for the Management of Patients with ST-Elevation Myocardial Infarction,", located at www.acc.org/guidelines/stemi/index/pdf, accessed on Aug. 10, 2005, pp. e1-e212.

(Continued)

*Primary Examiner*—Carl Layno
*Assistant Examiner*—Yun Haeng Lee
(74) *Attorney, Agent, or Firm*—Morrison & Foerster LLP

(57) ABSTRACT

The invention relates to the analysis of ECG data by exploiting computerized three-dimensional spatial presentation of the measured data using the vector concept. A three-dimensional presentation of the human heart may be correlated with waveforms specific for standard ECG or derived ECG signals based on the dipole approximation of the heart electrical activity. The three-dimensional heart model may be rotated, and the ECG signals are interactively linked to the model. In the visualization process, different types of signal presentation may be used, including graphical presentation of the heart vector hodograph, graphical presentation of the signal waveform in an arbitrary chosen point on the heart, and graphical presentation of the map of equipotential lines on the heart in a chosen moment. Additional tools for analyzing ECG data are also provided which may be interactively used with the display tools.

9 Claims, 16 Drawing Sheets

OTHER PUBLICATIONS

Braunwald, E. et al. (Oct. 2, 2002). "ACC/AHA 2002 Guideline Update for the Management of Patients with Unstable Angina and Non-ST-Segment Elevation Myocardial Infarction-Summary Article," *Journal of the American College of Cardiology* 40(7):1366-1374.

Burger, H.C. et al. (1948). "Heart-Vector and Leads. Part III. Geometrical Representation," *British Heart Journal* 10:229-233.

Cain, M.E. et al. (Jan. 1996). "Signal Averaged Electrocardiography: ACC Expert Consensus Document," *Journal of the American College of Cardiology* 27(1):238-249.

Edenbrandt, L. et al., (1988). "Vectorcardiogram Synthesized From a 12-Lead ECG: Superiority of the Inverse Dower Matrix," *Journal of Electrocardiology* 21(4):361-367.

Fisch, C. (Nov. 15, 2000). "Centennial of the String Galavanometer and the Electrocardiogram," *Journal of the American College of Cardiology* 36(6):1737-1745.

Frank, E. (May 1956). "An Accurate, Clinically Practical System for Spatial Vectorcardiography," *Circulation* 13:737-749.

Hurst, J.W. (Jun. 1997). "Abnormalities of the S-T Segment—Part I," *Clin. Cardiol.* 20(6):511-520.

Hurst, J.W. (Jan. 2000). "Methods Used to Interpret the 12-Lead Electrocardiogram: Pattern Memorization Versus the Use of Vector Concepts," *Clin. Cardiol.* 23(1):4-13.

Kors, J.A. et al. (Dec. 1990). "Reconstruction of the Frank Vectorcardiogram from Standard Electrocardiographic Leads: Diagnostic Comparison of Different Methods," *Eur. Heart. J.* 11(12):1083-1092.

Lee, T.H. et al. (2000). "Evaluation of the Patient with Acute Chest Pain," *N. Engl. J. Med.* 342(16):1187-1195.

Levkov, C.L. (Mar. 1987). "Orthogonal Electrocardiogram Derived from the Limb and Chest Electrodes of the Conventional 12-Lead System," *Medical and Biological Engineering and Computing* 25:155-164.

McCarthy, B.D. et al. (Mar. 1993). "Missed Diagnoses of Acute Myocardial Infarction in the Emergency Department: Results from a Multicenter Study," *Annals of Emergency Medicine* 22(3):579-582.

McMechan, S.R. et al. (1995). "Body Surface ECG Potential Maps in Acute Myocardial Infarction," *J. Electrocardiol.* 28 Suppl.:184-190.

Mehta, R.H. et al. (2000). "Missed Diagnoses of Acute Coronary Syndromes in the Emergency Room—Continuing Challenges," *N Engl J Med* 342(16):1207-1210.

Morikawa, J. et al. (Jun. 1987). "Three-Dimensional Vectorcardiography (3-D VCG) By Computer Graphics in Old Myocardial Infraction," *Angiology* 38(6):449-456.

Morikawa, J. et al. (Nov. 1996). "Delineation of Premature P Waves on Four-Dimensional Electrocardiography, a New Display of Electrical Forces By Computer Techniques," *Angiology* 47(11):1101-1106.

Niederberger, M. et al. (1977). "A Global Display of the Heart Vector (Spherocardiogram). Applicability of Vector- and Polarcardiographic Infarct Criteria," *J. Electrocardiol.* 10(4):341-346.

Petterson, J. et al. (1995). "Increased Sensitivity for the Diagnosis of Healed Myocardial Infarction Using Vectorial Information in the 12-Lead ECG," *Journal of Electrocardiology* 28(3):169-175.

Pope, J.H. et al. (2000). "Missed Diagnoses of Acute Cardiac Ischemia in the Emergency Department," *N Engl J Med* 342(16):1163-1170.

Rosamond, W.D. et al. (Sep. 24, 1998). "Trends in the Incidence of Myocardial Infarction and in Mortality Due to Coronary Heart Disease, 1987 to 1994," *N. Engl. J. Med.* 339(13):861-867.

Sada, T. et al. (1982). "Polarcardiographic Study Inferior Myocardial Infarction: Global Projection of Heart Vector," *J. Electrocardiol.* 15(3):259-264.

Titomir, L.I. et al. (May 1987). "Chronotopocardiography: A New Method for Presentation of Orthogonal Electrocardiograms and Vectorcardiograms," *Int. Bio-Medical Computing* 20(4):275-282.

Van Oosterom, A. (1997). "Incorporation of the Spatial Covariance in the Inverse Problem," *Biomedizinische Technik.* 42-E1:33-36.

\* cited by examiner

DEVICE AND PROCEDURE FOR VISUAL THREE-DIMENSIONAL PRESENTATION OF ECG DATA

CROSS-REFERENCE TO RELATED APPLICATIONS

This patent claims priority to Serbia and Montenegro patent P-43/04, filed Jan. 16, 2004, which is herein incorporated by reference in its entirety.

BACKGROUND OF THE INVENTION

1. Technical Field

The present invention relates to the field of medical electronics. In particular, it concerns electronic devices for acquisition and presentation of diagnostic data. The invention comprises devices and procedures for acquisition and analysis of electrocardiographic (ECG) data and the three-dimensional visualization of ECG data that enables more precise diagnostic interpretation of the ECG data. According to the International Patent Classification (IPC), the invention is categorized within the A61B 5/00 class, which defines methods or devices for measurement or recording in diagnostic purposes. More precisely, the invention is categorized within the A61B 5/04 class, which defines instruments for measuring or recording bioelectric charges of a body or an organ, such as electrocardiographs.

2. Technical Problem

Although the ECG is a universally accepted diagnostic method in cardiology that dates from the beginning of the 20th century, the major problem of modern electrocardiography is the lack of cardiologists experienced in interpreting ECG recordings (Fisch, C., Centennial of the string galvanometer and the electrocardiogram, *J. Am. Coll. Cardiol.*, 2000 Nov. 15; 36(6) 1737-45). Frequent mistakes are made in interpreting ECGs, because the most common approach for interpretation of ECGs is based on memorization of waveforms, rather than using vector concepts and basic principles of electrocardiography (Hurst, J. W., Methods used to interpret the 12-lead electrocardiogram: Pattern memorization versus the use of vector concepts, *Clin. Cardiol* 2000 January; 23(1):4-13). One embodiment of this invention simplifies the vector interpretation concept, and provides a visual three-dimensional presentation of a patient's ECG signal with a three-dimensional model of the human heart, rather than relying on the cardiologist's individual spatial imagination skills. The present invention exploits a dipole approximation of electrical heart activity, in keeping with the basis of the conventional doctrine of ECG interpretation.

Another problem with traditional ECG recordings is that the ECG may not provide adequate indications of electrical activity of certain regions of the heart, especially the posterior region. An embodiment of this invention provides a more accurate approximation of cardiac activity, particularly for regions of the heart, such as the posterior region, that generally were less well represented using prior ECG recordings, and may also provide greater indications of cardiac events such as ischemia.

Furthermore, prior analysis of ECG recordings required a substantial amount of training and familiarity with reading of the recorded waveforms. An embodiment of this invention provides analysis tools to aid in the interpretation of cardiac electrical activity.

3. Background Art

There have been many attempts to extract additional information from the standard 12-lead ECG measurement when measuring the electric potential distribution on the surface of the patient's body for diagnostic purposes. These attempts have included new methods of measured signal interpretation, either with or without introducing new measurement points, in addition to the standard 12-lead ECG points. All of these are attempts to improve the spatial (i.e., the three-dimensional) aspect of interpretation.

These attempts have been conducted in several directions, including Vector ECG (VCG), modification of VCG, Electrocardiographic mapping, and Inverse Epicardiac Mapping.

Vector ECG

VCG is the oldest approach that includes the improvement of a spatial aspect to the ECG (Frank, E, An Accurate, Clinically Practical System For Spatial Vectorcardiography, *Circulation* 13: 737, May 1956). Like conventional ECG interpretation, VCG uses a dipole approximation of electrical heart activity. The dipole size and orientation are presented by a vector that continuously changes during the heartbeat cycle. Instead of presenting signal waveforms from the measurement points (waveforms), as it is the case with standard 12-lead ECGs, in VCG, the measurement points are positioned in such a way that three derived signals correspond to three orthogonal axes (X, Y, Z), and these signals are presented as projections of the vector hodograph onto three planes (frontal, sagittal, and horizontal). In this way, VCG represents a step towards spatial presentation of the signal, but the cardiologist's spatial imagination skills were still necessary to interpret the ECG signals, particularly the connection to the heart anatomy. Furthermore, a time-dependence aspect (i.e., the signal waveform) is lost with this procedure, and this aspect is very important for ECG interpretation. VCG introduces useful elements which cannot be found within the standard 12-lead ECG, however, the incomplete spatial presentation and loss of the time-dependence are major reasons why VCG, unlike ECG, has never been widely adopted, despite the fact that (in comparison to ECG) VCG can more often correctly diagnose cardiac problems, such as myocardial infarction.

Modifications of Vector ECG

There have been numerous attempts to overcome the drawbacks of the VCG method described above. These methods exploit the same signals as VCG (X, Y, Z), but their signal presentation is different than the VCG projection of the vector hodograph onto three planes:

"Polarcardiogram" uses Aitoff cartographic projections for the presentation of the three-dimensional vector hodographs (Sada, T., et al., Polarcardiographic study of inferior myocardial infarction: global projection of heart vector, *J. Electrocardiol.* 1982; 15(3):259-64).

"Spherocardiogram" adds information on the vector amplitude to the Aitoff projections, by drawing circles of variable radius (Niederberger, M., et al., A global display of the heart vector (spherocardiogram). Applicability of vector—and polarcardiographic infarct criteria, *J. Electrocardiol.* 1977; 10(4):341-6).

"3D VCG" projects the hodograph onto one plane, which is chosen as the most suitable for establishing a diagnosis (Morikawa, J., et al., Three-dimensional vectorcardiography (3-D VCG) by computer graphics in old myocardial infarction. *Angiology*, 1987 June; 38(6):449-56).

"Four-dimensional ECG" is similar to "3D VCG," but differs in that every heartbeat cycle is presented as a separate loop, where the time variable is superimposed on one of the spatial variables (Morikawa, J., et al., Delineation of premature P waves on four-dimensional electrocardiography, a new display of electrical forces by computer techniques, *Angiology,* 1996 November; 47(11):1101-6.).

"Chronotopocardiogram" displays a series of heart-activity time maps projected onto a sphere (Titomir, L. I., et al., Chronotopocardiography: a new method for presentation of orthogonal electrocardiograms and vectorcardiograms, Int J Biomed Comput 1987 May; 20(4):275-82).

None of these modifications of VCG been widely accepted in diagnostics, although they have some improvements over VCG.

Electrocardiographic Mapping

Electrocardiographic mapping is based on measuring signals from a number of measurement points on the patient's body (usually 25 to 200 points). Signals are presented as maps of equipotential lines on the patient's torso (Mc-Mechan, S. R., et al., Body surface ECG potential maps in acute myocardial infarction, *J. Electrocardiol.* 1995; 28 Suppl:184-90). This method provides significant information on the spatial dependence of electrocardiographic signals. The drawback of this method, however, is a prolonged measurement procedure in comparison to ECG, and a loose connection between the body potential map and heart anatomy.

Inverse Epicardiac Mapping

Inverse epicardiac mapping includes different methods with different names, but these methods have a few things in common: they all use the same signals for input data as those used in ECG mapping; and they are all based on numerically solving the so-called inverse problem of electrocardiography (A. van Oosterom, Incorporation of the Spatial Covariance in the Inverse Problem, *Biomedizinisch Technik.,* vol. 42-E1, pp. 33-36, 1997). As a result, distributions of the electric potentials on the heart are obtained. These methods are very complicated, and are still being developed, and, so far, have not resulted in useful clinical devices.

All the methods described above only partially solve the problem of the spatial aspect of ECG interpretation, and all of them impose the introduction of new criteria, i.e., a new doctrine of interpretation, into cardiologic diagnostics.

BRIEF SUMMARY OF THE INVENTION

The devices and procedures described herein solve these technical problems by providing normalized ECG data that may be presented visually in three dimensions.

The present invention provides computer normalized cardiac electrical signals that may be correlated with a three-dimensional presentation of the human heart, while simultaneously maintaining the correlation with the waveforms derived from a standard ECG.

Described herein is a method for analyzing cardiac electrical activity comprising: obtaining ECG data measured from a plurality of actual lead sites on the surface of a patient's body; computing from the ECG data measured at the plurality of actual lead sites, a time variable heart vector that represents size and orientation of a time varying electrical dipole that approximates electrical heart activity and that has an origin near the center of the patient's heart; and normalizing the time variable heart vector by a normalization factor without changing the direction of the time variable heart vector, wherein the normalization factor is computed from the patient's ECG data.

In some versions, the method further comprises: selecting a position corresponding to a virtual lead; and producing information concerning electrical potential corresponding to the selected position by scalar multiplication of the produced normalized time variable heart vector and a lead vector that corresponds to the selected position.

A cardiac electrical signal may be derived from the normalized time variable heart vector. Cardiac electrical signals may be displayed using a representation of a three dimensional image of a model heart. Actual lead sites may include standard ECG lead sites. Components of the time variable heart vector may be computed as a linear combination of the ECG data measured at a minimum of three actual lead sites. Normalizing the time variable heart vector may comprise normalizing the heart vector to a normalization surface having a selected attenuation value.

A Normalization factor may be computed by computing a lead normalization factor, $\rho_i$, for an actual lead site according to the ratio:

$$\rho_i = \frac{\int_0^T V_i(t) \cdot [\vec{H}(t) \cdot \vec{L}_i] dt}{\int_0^T [\vec{H}(t) \cdot \vec{L}_i]^2 dt}$$

wherein $v_i(t)$ is the measured voltage over time from an actual lead site, $\vec{H}(t)$ is the time variable heart vector, $\vec{L}_i$ is a lead vector corresponding to the actual lead site, and T is a time period. Computing a normalization factor may comprise: computing lead normalization factors from a plurality of actual lead sites; and selecting a normalization factor from within the range defined by the maximum and the minimum lead normalization factors computed for the plurality of actual lead sites. Selecting a normalization factor from within the range defined by the maximum and the minimum lead normalization factors computed for the plurality of actual lead sites may include selecting the average value of the plurality of lead normalization factors. The time, period, T, may include the time period during which ECG data was measured at the plurality of actual lead sites on the surface of a patient's body. The lead normalization factors may be calculated for the precordial leads.

A time-dependent voltage, V1, may be calculated from the scalar product of a lead vector and the normalized time variable heart vector for a point selected from a virtual sphere centered around the patient's heart.

A cardiac electrical signal may be derived from the normalized time variable heart vector. The cardiac electrical signal may be displayed using a representation of a three dimensional image of a model heart. A user may select the display format of the cardiac electrical signal, wherein the user may choose to display the cardiac electrical signal as a heart vector, a vector loop hodograph, an equipotential plot, an ECG waveform, or some combination of these.

Producing information concerning electrical potential corresponding to the designated position may include producing information concerning electrical potential from at least an ST portion of an ECG waveform corresponding to the designated position on the heart representation.

The method for analyzing cardiac electrical activity may also include: selecting a first time corresponding to a first point in the heart cycle; selecting a second time corresponding to a second point in the heart cycle; and producing information concerning a heat vector spatial angle from the time variable heart vector at the first time and the time variable heart vector at the second time.

Also described herein are devices for analyzing cardiac electrical activity comprising: a data input for obtaining ECG data measured from a plurality of sites on the surface of a patient's body; a signal processing module for computing a normalized time variable heart vector that represents size and orientation of a time varying electrical dipole approximating the electrical activity of a patient's body, wherein the normalized time variable heart vector is normalized by a normalization factor without changing the direction of the time variable heart vector, wherein the normalization factor is computed from the patient's ECG data; and an output for reporting a processed normalized time variable heart vector.

Also described herein are methods for analyzing cardiac electrical activity comprising: obtaining ECG data measured from a plurality of actual lead sites on the surface of a patient's body; computing from the ECG data measured at the plurality of actual lead sites, a time variable heart vector that represents size and orientation of a time varying electrical dipole that approximates electrical heart activity and that has an origin near the center of the patient's heart; selecting a first time corresponding to a first point in the heart cycle from an ECG signal waveform; selecting a second time corresponding to a second point in the heart cycle from an ECG signal waveform; and producing information concerning a heat vector spatial angle from the time variable heart vector at the first time and the time variable heart vector at the second time.

Also described are methods of detecting of ischemia comprising: computing from patient-specific ECG data measured at the plurality of actual lead sites, a time variable heart vector that represents size and orientation of a time varying electrical dipole that approximates electrical heart activity and that has an origin near the center of the patient's heart; normalizing the time variable heart vector by a normalization factor without changing the direction of the time variable heart vector, wherein the normalization factor is computed from the patient's ECG data; calculating a normalized ST-segment vector magnitude from the time variable heart vector; and providing information about the ischemia by comparing the normalized ST-segment vector magnitude to an ST-segment ischemia criterion. In some versions, of this method, the ST-segment ischemia criterion is 0.1 mV.

Also described herein are methods for visualizing cardiac electrical activity comprising: obtaining ECG data measured from a plurality of actual lead sites on the surface of a patient's body; computing from the ECG data measured at the plurality of actual lead sites, a time variable heart vector that represent size and orientation of a time varying electrical dipole that approximates electrical heart activity and that has an origin near the center of the patient's heart; normalizing the time variable heart vector by a normalization factor, wherein the normalization factor is computed from the patient's ECG data; deriving a cardiac electrical signal from the normalized time variable heart vector; and displaying the cardiac electrical signal using a representation of a three dimensional image of a model heart.

A user may select the display format of the cardiac electrical signal, and may choose to display the cardiac electrical signal as a heart vector, a vector loop hodograph, an equipotential plot, an ECG waveform, or some combination of these. The actual lead sites may include standard ECG lead sites. The components of the time variable heart vector may be computed as a linear combination of the ECG data measured at a minimum of three actual lead sites.

Normalizing the time variable heart vector may comprise computing a lead normalization factor, $\rho_i$, for each of one or more actual lead sites, according to the ratio:

$$\rho_i = \frac{\int_0^T V_i(t) \cdot \left[\vec{H}(t) \cdot \vec{L}_i\right] dt}{\int_0^T \left[\vec{H}(t) \cdot \vec{L}_i\right]^2 dt}$$

wherein $v_i(t)$ is the measured voltage over time from an actual lead site, $\vec{H}(t)$ is the time variable heart vector, $\vec{L}_i$ is the lead vector pointing in the direction of the actual lead site, and T is a time period; and selecting a normalization factor from within the range defined by the maximum and the minimum lead normalization factors computed for the one or more actual lead sites; scaling the magnitude of the time variable heart vector at all time by the normalization factor.

In some versions, selecting a normalization factor from within the range defined by the maximum and the minimum lead normalization factors computed for the one or more actual lead sites comprises selecting the average of the one or more lead normalization factors. The lead normalization factors may be calculated for the precordial leads. Deriving a cardiac electrical signal from the normalized heart vector may include selecting a time range and deriving a three dimensional heart vector hodograph over the time range. Deriving a cardiac electrical signal from the normalized heart vector may include deriving a time-dependent voltage, $V_1$, from the scalar product wherein:

$$V_1 = l_x * X' + l_y * Y' + l_z * Z'$$

where $l_x$, $l_y$ and $l_z$ are components of a lead vector L at a selected point on a virtual sphere centered around the patient's heart, and wherein X', Y', Z' are components of the normalized time variable heart vector.

In some versions, the method further comprises: selecting a point on the surface of the model heart; indicating the location of the selected point on the image of the model heart; and displaying the cardiac electrical signal, $V_1$, derived from the normalized heart vector that is correlated to the selected point, wherein the cardiac electric signal comprises an ECG waveform. The method may also include displaying an ECG waveform measured from one of said actual lead site on the surface of a patient's body. In some versions, the method includes deriving a cardiac electrical signal from the normalized time variable heart vector comprises selecting a time point. Selecting the time point may comprise selecting a time point from an ECG waveform. Displaying the cardiac electrical signal on the image of the model heart may comprise displaying the normalized heart vector at the selected time point.

In some versions, the method for visualizing cardiac electrical activity also includes: selecting a time point; selecting a voltage threshold; displaying equipotential lines for voltages above or equal to the selected voltage threshold level on the image of the model heart, wherein the equipotential plot lines correspond to the cardiac electrical signal over the surface of the model heart at the selected time point. The method may also include allowing a user to rotate the model heart to display different perspective views of the model heart. The display may be in color. A portion of the model heart may be made transparent. A body-referenced coordinate system correlated to the model heart may also be displayed. The method may also include indicating on the model heart a location corresponding to the location of at least one of the conventional chest ECG measurement sites V1, V2, V3, V4, V5, V6, and special chest ECG measurement sites V3R, V4R, V5R, V6R, V7, V8, V9 from the surface of the patient's body.

The three dimensional model heart may include anatomical heart features.

Also described are devices for visualizing cardiac electrical activity comprising: a data input for obtaining ECG data measured from a plurality of sites on the surface of a patient's body; a signal processing module for generating a model heart and deriving a normalized heart vector from the patient's ECG data; a display for displaying the cardiac electrical signal using a representation of a three dimensional image of the model heart; and a user input for allowing a user to select the perspective view of the model heart and the corresponding cardiac electrical signal.

Also described herein are methods of analyzing cardiac electrical activity comprising: obtaining ECG data measured at a plurality of actual lead sites on the surface of a patient's body; computing from the ECG data measured at the plurality of actual lead sites, a time variable heart vector that represents size and orientation of a time varying electrical dipole that approximates electrical heart activity and that has an origin near the center of the patient's heart; computing a normalization factor from the ECG data measured at the plurality of actual lead sites; and producing information concerning a normalized time variable heart vector by scaling the time variable heart vector by the normalization factor. In some versions, this method also includes: selecting a position corresponding to a virtual lead; and producing information concerning electrical potential corresponding to the selected position by scalar multiplication of the produced normalized time variable heart vector and a lead vector that corresponds to the selected position. The actual lead sites may include standard ECG lead sites. The actual lead sites may include precordial ECG lead sites.

Computing a normalization factor may also comprise: computing lead normalization factors from a plurality of actual lead sites; and selecting a normalization factor from within the range defined by the maximum and the minimum lead normalization factors computed for the plurality of actual lead sites. Selecting a normalization factor from within the range defined by the maximum and the minimum lead normalization factors computed for the plurality of actual lead sites may include selecting the average value of the plurality of lead normalization factors.

The time period, T, may include the time period during which ECG data was measured at the plurality of actual lead sites on the surface of a patient's body.

Also described herein are methods of displaying cardiac electrical activity comprising: obtaining ECG data measured at a plurality of actual lead sites on the surface of a patient's body; computing from the ECG data measured at the plurality of actual lead sites, a time variable heart vector that represents size and orientation of a time varying electrical dipole that approximates electrical heart activity and that has an origin near the center of the patient's heart; computing a normalization factor from the ECG data measured at the plurality of actual lead sites; computing a normalized time variable heart vector by scaling the time variable heart vector by the normalization factor; producing a three dimensional heart representation on a display screen having the same origin as the time variable heart vector; indicating on the display screen a designated position on the heart representation; and producing information concerning electrical potential corresponding to the designated position by scalar multiplication of the normalized time variable heart vector and a lead vector that corresponds to the selected position.

In some versions, the method of displaying cardiac electrical activity may further comprise indicating on the display screen a designated position on the heart representation includes displaying on the display screen a marker on the heart representation at the designated position. The position to be indicated may also be designated on the heart representation.

In some versions, the method may include displaying on the display screen the produced information concerning electrical potential corresponding to the designated position. The method may also include displaying on the display screen the produced information concerning electrical potential corresponding to the designated position together with the heart representation with the indicated position.

Producing information concerning electrical potential corresponding to the designated position may include producing information concerning electrical potential for a designated temporal position of an ECG waveform corresponding to the designated position on the heart representation. Producing information concerning electrical potential corresponding to the designated position may include producing information concerning electrical potential from at least an ST portion of an ECG waveform corresponding to the designated position on the heart representation. Producing information concerning electrical potential corresponding to the designated position may include producing information concerning at least an ST portion of an ECG waveform corresponding to the designated position on the heart representation; and may further include displaying on the display screen at least a portion of the ST portion of the ECG waveform corresponding to the designated position on the heart representation.

In some versions, the method further includes: selecting a time instant; and indicating on the display screen a heart vector corresponding to the designated position at the selected time instant. The method may also include: selecting a time instant; producing information concerning the electrical potential over the heart representation by scalar multiplication of the normalized heart vector at the selected time instant and the lead vectors that corresponds to the heart representation; indicating on the display screen an equipotential plot on the heart representation for the selected time instant.

In some versions, the method includes: selecting a threshold voltage; selecting a time instant; producing information concerning the electrical potential over the heart representation by scalar multiplication of the normalized heart vector at the selected time instant and the lead vectors that corresponds to the heart representation; indicating on the display screen an equipotential plot on the heart representation showing electrical potentials above or equal to the absolute value of the selected threshold voltage at the selected time instant. The three dimensional heart representation may include anatomical heart features. A portion of the three dimensional heart representation may be made transparent. A body referenced coordinate system correlated to the heart representation may be indicated on the display screen. A three dimensional vector loop hodograph corresponding to the heart vector may be indicated on the display screen, wherein the vector loop hodograph is indicated on the heart representation.

In some versions, the method of displaying cardiac electrical activity may include: selecting a time instant; and indicating on the display screen a heart vector corresponding to the selected time instant, wherein the heart vector is indicated on the heart representation. The method may include: selecting a time instant from an ECG waveform;

indicating on the display screen a heart vector corresponding to the selected time instant, wherein the heart vector is indicated on the heart representation. A location corresponding to the location of at least one of the actual lead sites from the surface of the patient's body may be indicated on the heart representation on the display screen.

Also included is an article of manufacture encoded with computer readable information produced by the method including: obtaining ECG data measured at a plurality of actual lead sites on the surface of a patient's body; computing from the ECG data measured at the plurality of actual lead sites, a time variable heart vector that represents size and orientation of a time varying electrical dipole that approximates electrical heart activity and that has an origin near the center of the patient's heart; computing a normalization factor from the ECG data measured at the plurality of actual lead sites; and producing information concerning a normalized time variable heart vector by scaling the time variable heart vector by the normalization factor.

In some versions, the article of manufacture further comprises: selecting a position corresponding to a virtual lead; and producing information concerning electrical potential corresponding to the selected position by scalar multiplication of the produced normalized time variable heart vector and a lead vector that corresponds to the selected position.

Also described herein are systems using ECG data measured at a plurality of actual lead sites on the surface of a patient's body to produce a representation of cardiac electrical activity on a display screen, the system comprising: a signal processing module for computing a time variable heart vector from the ECG data measured at the plurality of actual lead sites, wherein the heart vector represents size and orientation of a time varying electrical dipole that approximates electrical heart activity and that has an origin near the center of the patient's heart; further where the signal processing module computes a normalized heart vector from the heart vector and a normalization factor, wherein the normalization factor is calculated from the ECG data measured at the plurality of actual lead sites; an interactive visualization module comprising: a display screen, wherein the visualization module produces a three dimensional heart representation on the display screen, wherein the heart representation is oriented in the same coordinates as the heart vector; an input for indicating on the display screen a designated position on the heart representation; further, wherein the signal processing module produces information concerning an electrical potential corresponding to the designated position by scalar multiplication of the normalized heart vector and a lead vector that corresponds to a position on the heart representation.

Also described herein are methods of detecting ischemia from cardiac electrical activity comprising: obtaining ECG data measured at a plurality of actual lead sites on the surface of a patient's body; computing from the ECG data measured at the plurality of actual lead sites, a time variable heart vector that represents size and orientation of a time varying electrical dipole that approximates electrical heart activity and that has an origin near the center of the patient's heart; computing a normalization factor from the ECG data measured at the plurality of actual lead sites; computing a normalized time variable heart vector by scaling the time variable heart vector by the normalization factor; selecting a time point during the ST-segment of an ECG waveform; and producing information about a normalized ST-segment vector magnitude by applying the calculation sqrt $(X^2+Y^2+Z^2)$, where X, Y, and Z are components of the normalized heart vector at the selected time point. Selecting the time point during the ST-segment may comprise selecting the J+80 point. Actual lead sites may include standard ECG lead sites, or precordial ECG lead sites.

In some versions, the method also includes: comparing the normalized ST-segment vector magnitude to a criterion for ischemia; and producing information about ischemia based on the comparison. The criterion for ischemia may be greater than about 0.1 mV.

Also described herein is a display depicting cardiac electrical activity in a heart comprising: a three dimensional heart representation; a marker shown on the surface of the three dimensional heart representation, wherein the marker may be moved on the surface of the three dimensional heart representation to select a spatial position; an ECG signal waveform showing an ECG signal computed at the selected spatial position from a normalized time variable heart vector that represents size and orientation of a time varying electrical dipole that approximates electrical heart activity and that has an origin near the center of the patient's heart, wherein the normalized heart vector is computed from ECG data measured at a plurality of actual lead sites on the surface of a patient's body; further wherein the normalized time variable heart vector is normalized by: computing a normalization factor from the ECG data measured at the plurality of actual lead sites; and scaling the time variable heart vector by the normalization factor.

Also described herein are articles of manufacture including computer readable medium encoded with an information structure produced by a method comprising: obtaining ECG data measured at a plurality of actual lead sites on the surface of a patient's body; computing from the ECG data measured at the plurality of actual lead sites a time variable heart vector that represents size and orientation of a time varying electrical dipole that approximates electrical heart activity and that has an origin near the center of the patient's heart; computing a normalization factor from the ECG data measured at the plurality of actual lead sites; producing information concerning a normalized time variable heart vector by scaling the time variable heart vector by the normalization factor; selecting a position corresponding to a virtual lead; and producing information concerning electrical potential corresponding to the selected position by scalar multiplication of the produced normalized time variable heart vector and a lead vector that corresponds to the selected position; and associating the selected virtual lead position with the produced information.

The device may have three modules: one for acquisition, one for processing, and one for visualization of the data.

A data acquisition module may perform the function of measuring and A/D (analog/digital) conversion of the signal, i.e., it performs the acquisition of the standard ECG signal.

A signal processing module may perform filtering, elimination of the base level fluctuation, and conversion of the 12 standard ECG leads into three orthogonal vector leads (X, Y, and Z).

A visualization module may use a computer screen and enable the presentation of the derived signals in a way that is suitable for perceiving the spatial aspect of a diagnosis. The base for the presentation is a three-dimensional model of the human heart which can be rotated and made transparent. The presented signal is correlated to the model and may rotate together with it.

The obtained cardiac electrical signal may be presented in at least three ways:

A graphical presentation of a heart vector hodograph on a three-dimensional heart model, A graphical presentation of the signal waveform from an arbitrarily chosen point on the heart model, A graphical presentation of the map of the equipotential lines on the heart model in the chosen moment.

Any of these representations may be shown, including a chosen standard ECG lead (waveform), a three-dimensional model of the heart, and a "virtual" (simulated) ECG waveform. These displays may be correlated, so that changes made to one display are reflected in the other displays. For example, selecting a time point from an ECG waveform may cause the electrical activity at that time point to be displayed on the heart model, and selecting a point from the heart model may change the waveform display to show an ECG waveform derived for that position.

Using the described procedure of presenting cardiac electrical data, the cardiologist does not need to rely on his spatial imagination skills when interpreting ECGs, since a direct three-dimensional presentation is provided on a screen. At the same time, this inventive method of presenting cardiac data and the standard ECG waveform may be simultaneously used. Furthermore, a major drawback of vector ECG, related to the loss of the time axis (i.e., the waveform) in the spatial presentation of the data, is also eliminated.

Another important advantage of the invention is the fact that, unlike some methods introduced earlier (such as "spherocardiogram" and "four-dimensional ECG") that suggest new diagnostic criteria, the inventive method uses diagnostic criteria that have been accepted within the diagnostics of standard ECG analysis; the invention makes the use of these standard diagnostics easier, aiding the interpretation of ECG results.

DETAILED DESCRIPTION OF THE INVENTION

Figure 1:
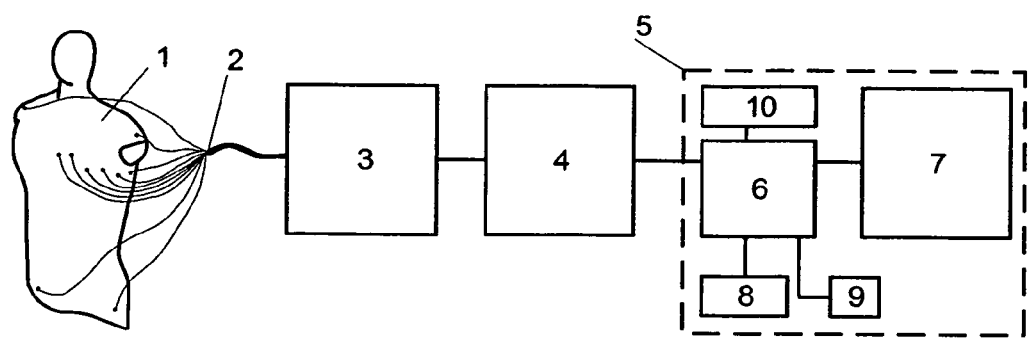
FIG. 1 shows a block diagram of one version of the device for three-dimensional presentation of ECG data described herein.

The devices, systems, articles of manufacture, and methods descried herein allow display and analysis of the electrical activity of a heart by processing cardiac ECG data and by providing different types of analytic tools, including computerized three-dimensional spatial presentations of ECG data recorded from a patient. ECG data is provided, processed, and displayed. Data processing and display may be interactively performed by allowing a user to select different data analysis and display parameters. Cardiac electrical signals derived from the provided ECG data may be displayed as a three-dimensional representation on a model heart; this three-dimensional representation may be manipulated by a user, and may be correlated with two-dimensional representations of cardiac electrical signals, such as standard ECG waveforms. Thus, the cardiac electrical signals may be visualized spatially and temporally. Furthermore, cardiac electrical signals may be analyzed with a variety of tools described herein that may simplify or enhance the analysis of cardiac electrical activity. The ECG analyzer described herein may be used to analyze ECG data as described herein.

A. Acquisition of ECG Data

Any appropriate source of patient ECG data may be used. For example, ECG data may be recorded directly from a patient, or it may be provided from stored, previously recorded data. Thus, the present invention may use real-time ECG data, or ECG data from archived sources.

ECG data may be of any appropriate type. ECG data may be recorded from a plurality of lead sites on the surface of the patient's body. In some versions, standard 12-lead ECG recordings are provided (e.g., leads I, II, III, aVR, aVF, aVL, V1, V2, V3, V4, V5 and V6). Any appropriate number of ECG leads, positioned at any appropriate body sites, may be used. Examples of other ECG lead systems include the "Frank" electrode lead system (e.g., 7 electrodes), the McFee-Parungao Lead System, the SVEC III Lead System, Fischmann-Barber-Weiss Lead System, and the Nelson Lead System. Other examples include addition of right-sided precordial leads, posterior leads, leads placed in higher or lower intercostal spaces, and the like. Although the examples of ECG data described herein refer to the standard 12-lead system, it should be understood that any appropriate ECG lead system may be used without altering the basic principles of the invention. In some versions, information about the source of the ECG data may be provided to the ECG analyzer. For example, the ECG analyzer may adapt the configuration of the display and/or analysis tools based on the source of the ECG data, such as the position of the ECG leads with respect to the heart, the body, and/or to other leads.

Different amounts of ECG data may also be provided. For example, an ECG waveform may contain multiple repeated "PQRST" waveforms. In some versions, multiple cycles of PQRST (e.g., describing multiple heartbeats) may be provided. However, as few as a single PQRST (e.g., a single heartbeat) cycle, or even a portion of one cardiac cycle, may be used. In other versions, signal-averaged ECG waveforms (Signal-Averaged Electrocardiography: Expert Consensus Document, J Am Coll Cardiol 1996; 27: 238-49) may be used.

Additional patient data may also be provided, including patient statistics (height, weight, age, etc.), vital signs, medical history, physical exam findings (for example, extra heart sounds, rubs, or murmurs) and the like. Such patient data may be used in conjunction with patient-specific ECG data for data processing and display, or it may be used to correlate information extracted from the ECG data. For example, the orientation of the heart may be calculated based on patient-specific data (e.g., height, weight, torso circumference, etc.) and may be used to orient the heart model and other analytic features.

ECG Analyzer

Data may be acquired by the ECG analyzer or it may be obtained from another source (e.g., an ECG recorder, etc.). As used herein, "obtaining ECG data" refers to any appropriate method of obtaining or receiving ECG data, including, but not limited to, directly measuring ECG data, reading ECG data from a recorded (e.g., archived) source, and receiving ECG data from another device. In some versions, the ECG analyzer comprises an acquisition module. An acquisition module may "condition" (or "precondition") data that it receives. For example, an acquisition module may filter, amplify, format, or otherwise operate on ECG data provided from any source, including stored data sources. The ECG analyzer may also receive non-ECG data, including patient data. In some versions, an acquisition module acquires ECG data by direct input from electrical leads connected to a patient.

B. Signal Processing

Patient ECG data may be processed and displayed. Analysis and visualization of the electrical activity of the heart may be simplified by approximating the electrical activity of the heart as an electric dipole. Thus, ECG data may be transformed into a heart vector representing the electrical phenomena in the heart. A heart vector may be defined by three orthogonal projections: X, Y, and Z. If the provided ECG data is not in the form of a heart vector, then the recorded ECG data (actual ECG data) may be used to compute a heart vector (e.g., from a standard 12-lead ECG). The heart vector may be used with a lead vector (approximating tissue attenuation) to calculate "virtual" ECG waveforms. Furthermore, the heart vector may be normalized by a normalization factor so that the resulting normalized heart vector, and any virtual ECG waveforms calculated from the normalized heart vector, may be used to accurately and precisely analyze the cardiac electrical activity of the heart.

1. Computation of the Heart Vector

ECG data provides a time-dependent voltage that reflects the electrical activity of the heart over time; multiple ECG lead sites provide different time-dependent voltage waveforms that reflect this overall electrical activity. Given the spatial location of the ECG leads, a single time-dependent heart vector may be computed by approximating the heart electrical activity as a dipole having an origin near the center of the patient's heart. A time-dependent heart vector that represents the size and orientation of the time-varying electrical dipole may be calculated by approximating the electrical activity of the heart.

As few as three leads (corresponding to four to six electrodes) may be used to obtain the X,Y,Z orthogonals of the heart vector. Given a set of leads, any appropriate matrix may be used to convert them to the X,Y,Z orthogonal components of the heart vector. For example, a heart vector may be calculated from standard 12-lead ECG data by transforming the 12-leads into X,Y,Z (e.g., Frank) leads. In one version, a conversion matrix may be used to transform the 12-lead ECG voltages into the three orthogonal components, X, Y, and Z. When converting 12-lead ECG data into a heart vector, an inverse Dower matrix may be used. Examples of the Dower matrix and the inverse Dower matrix may be found in U.S. Pat. Nos. 4,850,370 and 5,711,304, which are herein incorporated by reference in their entirety. Other types of matrices may be used to transform the ECG data (e.g., 12 lead ECG data) into a heart vector, such as a Levkov matrix (Levkov, C. L., Orthogonal electrocardiogram derived from the limb and chest electrodes of the conventional 12-lead system, *Med. Biol. Eng. Comput.* 1987, 25,155-164). Any appropriate means may be used to convert the ECG data into the heart vector. In some versions, a matrix or conversion paradigm could be derived, e.g., from experimental data. As used herein, unless the context makes it clear otherwise, a matrix is a set of linear equations that define a transformation between two sets of variables.

The heart vector is a dipole representation of the cardiac electrical signal of the heart, and may be calculated from recordings taken at some distance from the surface of the heart (e.g., from body surface electrodes, internal electrodes such as esophageal electrodes, and combinations of internal and external electrodes).

EXAMPLE 1

Calculation of a Heart Vector from Actual ECG Data

For example, a heart vector may be calculated from 8 standard ECG leads (recorded at leads I, II, $V_1$, $V_2$, $V_3$, $V_4$, $V_5$, and $V_6$). In this example, an Inverse Dower matrix is used to convert the data from the standard leads into the time variable heart vector that represents the size and orientation of a time varying electrical dipole approximating the electrical current (and voltage) of the heart.

The heart vector is described by $\vec{H}$:

$$\vec{H}=(X,Y,Z)=X\vec{i}+Y\vec{j}+Z\vec{k} \tag{1}$$

The ECG data from eight independent ECG leads can be described as a vector, $\vec{V}$:

$$\vec{V}=(I, II, V_1, V_2, V_3, V_4, V_5, V_6) \tag{2}$$

leads I, II, $V_1$, $V_2$, $V_3$, $V_4$, $V_5$, and $V_6$ described the recorded potentials from the ECG recorded at the actual lead sites on the surface of a patient's body.

Using an Inverse Dower matrix (ID), the ECG data may be converted into the heart vector containing three orthogonal components, X,Y,Z. In this case, a reasonable Dower matrix is given by:

$$ID = \begin{vmatrix} .156 & -.00893 & -.173 & -.0747 & .122 & .231 & .239 & .194 \\ -.223 & .875 & .056 & -.018 & -.104 & -.0209 & .0408 & .0476 \\ .0225 & .101 & -.229 & -.310 & -.246 & -.0626 & .0550 & .109 \end{vmatrix} \tag{3}$$

This inverse Dower matrix (3×8) may be applied to ECG signals recorded from the standard positions of the leads (Pettersson et al., *J. Cardiol.* 28:169, 1995). From equations (2) and (3), the heart vector may be calculated by matrix multiplication:

$$\vec{H}=ID\cdot\vec{V} \tag{4}$$

which is equivalent (expressed as linear equations) to:

$$X=0.156\cdot I-0.00893\cdot II-0.173\cdot V_1-0.0747\cdot V_2+0.122\cdot V_3+0.231\cdot V_4+0.239\cdot V_5+0.194\cdot V_6 \tag{5}$$

$$Y=-0.223 \cdot I+0.875 \cdot II+0.056 \cdot V_1-0.018 \cdot V_2-0.104 \cdot V_3-0.209 \cdot V_4+0.0408 \cdot V_5+0.0476 \cdot V_6 \quad (6)$$

$$Z=0.225 \cdot I+0.101 \cdot II-0.229 \cdot V_1-0.310 \cdot V_2-0.246 \cdot V_3-0.0626 \cdot V_4+0.0550 \cdot V_5+0.109 \cdot V_6 \quad (7)$$

Thus, the X, Y, and Z components of the heart vector may be solved at any time point by applying the ECG data into these linear equations.

The dipole approximation of heart activity given by the heart vector offers an approximation of cardiac electrical activity, however the heart vector does not give the electrical activity at any particular body surface. For example, the cardiac electrical signals present in an ECG waveform are typically recorded from the surface of the body (or from some internal body sites some distance from the heart). Thus, electrical activity arising from the heart is attenuated by body tissues between the heart and the point of measurement. An empirically determined "lead vector" may therefore be used to estimate a "virtual" signal waveform (e.g., an ECG waveform) recorded anywhere around the heart.

2. Computation of Signal Waveforms at an Arbitrary Point from a Model Heart

In general, a heart vector and a lead vector may be used to derive an ECG signal waveform at any position around the heart. A lead vector, L, may be described by components $l_x$, $l_y$, and $l_z$. The magnitude of a lead vector describes the attenuation factor of body tissue between the source of the electrical phenomenon (the heart) and a "virtual" recording position (H. E. Burger, J. B. van Milaan, Heart Vector and Leads, Brit. Heart J. 10:229, 1948). For example, a lead vector describing the attenuation factors from the heart to points on the body surface may have magnitudes of different values corresponding to different attenuation factors (i.e. distances from the heart center). Thus, any appropriate lead vector may be used to derive virtual ECG recordings. In some versions, the lead vector may be determined based on empirical measurements. As used herein, unless the context makes clear otherwise, the term "lead vector" may refer to both a real electrode measurement (when the parameters of the electrode reflect the direction and attenuation of the signal at the measurement point), and a parameter of a virtual (or imaginary) measurement surface, defined by a direction and an attenuation factor for a point on the virtual surface.

The lead vector may have a direction corresponding to the position of the recording electrode (e.g., an actual recording electrode or a "virtual" recording electrode) on the body surface, and a magnitude approximately equal to some attenuation factor similar to the electrical attenuation between the heart and the surface of the body where the recording electrode would lie. Thus, by scalar multiplication, a cardiac electrical signal (e.g., an ECG waveform) may be determined for any virtual lead, and any position around the heart may be chosen as a virtual lead. For example, a point (virtual lead) may be selected from the surface of a heart model that is centered using the same coordinate origin as the heart vector and the lead vector. Any point around the heart model may be correlated to a lead vector having a direction including that point (e.g., $l_x$, $l_y$, and $l_z$ where x, y, and z describe the point). Thus, an arbitrary point selected from the heart model may generate a virtual ECG by scalar multiplication of the time-dependent heart vector and the lead vector having the spatial direction of that point.

The scalar product of the lead vector at that point and the heart vector gives the instantaneous potential of the ECG lead for that electrode position. This relationship may be represented by:

$$V_1 = l_x * X + l_y * Y + l_z * Z \quad (8)$$

Where $V_1$ is the time-dependent electric potential at an arbitrary point on the patient's body (the value of the recorded lead signal), $l_x$, $l_y$, $l_z$ are the components of the lead vector L from that arbitrary point on the body surface, and X, Y, and Z are the components of the heart vector, i.e., the values in three orthogonal vector leads as they have been defined previously.

Thus, a virtual ECG waveform calculated for a point on a body surface around the heart may be approximated by the scalar product of the heart vector and an attenuation factor (given by a lead vector) at that point.

Both the virtual (simulated) and actual (recorded) ECG waveforms reflect the voltage arising from the heart that is recorded at some point on the body surface. This electrical signal has passed from the heart, through the body tissue, and been attenuated depending upon where on the body surface the ECG waveform is recorded. Thus, it is difficult to accurately compare the magnitudes of electrical signals recorded (or simulated) at different points on the surface of the body to each other, or to an empirical electrical criterion (e.g., ST depression or elevation) useful for analyzing the heart. Furthermore, the magnitudes of derived heart vectors (e.g., Frank vectors) are typically undefined, and correspond only to an imaginary surface centered around the heart. However, the heart vector may be normalized such that the voltage (or current) from ECG waveforms simulated anywhere around the heart may be reliably compared with clinically relevant benchmarks.

3. Normalization of the Heart Vector

The heart vector may be normalized by any appropriate method allowing comparison of the normalized heart vector (or cardiac electrical signals derived from the normalized heart vector) to a clinically relevant benchmark. For example, the heart vector may be normalized by scaling the magnitude of the heart vector for all time by a normalization factor. The normalization factor may be derived from actual ECG data specific to each patient. The normalization factor may define a normalization surface (e.g., a sphere) which is centered at the origin of the heart vector. As used herein, the term "scaling" includes multiplying a vector a normalization factor so that the magnitude of the vector is multiplied by the normalization factor.

In general, the normalization factor is determined by minimizing the difference between actual and virtual voltages recorded at selected leads. Normalization only changes the magnitude (not the direction) of the heart vector.

The heart vector may be normalized so that the magnitude of the heart vector (or virtual ECG waveforms derived from the normalized heart vector) may be comparable to the magnitude of signals recorded from individual precordial leads or any combination of precordial leads. The precordial leads (e.g., leads $V_1$, $V_2$, $V_3$, $V_4$, $V_5$, $V_6$) are well characterized, and a number of clinically relevant benchmarks for cardiac phenomena have been derived from the magnitude of regions of ECG waveforms recorded from standard precordial sites (e.g., ST elevation/depression, R-wave magnitude, and the like). Thus, the leads chosen for normalization should correspond to leads whose recorded signals contribute to the establishment of the particular benchmark (or criterion) that will be used to analyze the virtual heart vector. Thus, although any lead may be used to normalize the heart vector (including non-precordial leads, such as the limb leads), leads that did not correspond to the establishment of the particular benchmark may negatively impact the normalization, and should not be included in normalization for that particular benchmark or criterion.

In one version, a normalization factor ($\rho$) is derived by first calculating an individual normalization lead factor ($\rho_i$) for each actual lead, i. Thus, if the six precordial leads are used to determine the normalization factor, an individual lead normalization factor ($\rho_i$) is calculated for each of the six precordial leads ($V_i$, where i=1 to 6), and the normalization factor $\rho$ is selected from the range defined by the maximum and minimum value of these six lead normalization factors.

In this example, each lead normalization factor ($\rho_i$) is calculated by solving for the minimum value of the least-squares difference between the actual ECG waveform over some time (T) and a virtual ECG waveform calculated from the heart vector at that point (by scalar multiplication to a lead vector, as described above), over the same time (T). In some versions, each lead normalization factor ($\rho_i$) is approximately equal to a value that sets the magnitude of a virtual ECG waveform generated using the scaled heart vector to approximately the same magnitude as the actual ECG waveform recorded at the same position around the heart (e.g., the same lead position). The normalization factor ($\rho$) is then selected from within the range of the individually calculated lead normalization factors ($\rho_i$).

Put another way, each lead normalization factor is approximately equal to the ratio (e.g., the least-squares difference) between a cardiac signal derived from the heart vector for a given lead over some time period (e.g., a "virtual" ECG signal recorded at a lead for 5 seconds), and an actual cardiac signal recorded at the same lead for the same time period of time. Thus, a lead normalization factor may be chosen so that error between the recorded and derived leads is minimized. In some versions, the normalization factor is chosen so that difference between the actual and derived leads recorded nearest the chest (e.g., the precordial leads) is minimized. Normalization factors calculated using the precordial leads are appropriate when using an analysis criterion based on a clinically relevant benchmark (e.g., voltage or current) measured for precordial electrodes or electrodes with comparable signals.

Thus, when calculating the normalization factor, a "virtual" signal waveform may be calculated from the heart vector at the position of an actual lead, as described in more detail above.

EXAMPLE 2

Calculation of a Normalization Factor

In this example, a normalization factor ($\rho$) is calculated using six standard precordial leads. $v_i(t)$ is the recorded voltage over time from a lead (e.g., the actual voltage from precordial leads 1 to 6, where i=1 to 6), and $Vd_i(t)$ is the derived voltage for each of the ECG leads (e.g., the same leads 1 to 6). As previously described, virtual lead voltages are calculated as a scalar product of the heart vector $\vec{H}$ and a lead vector, $\vec{L}_i$, $$Vd_i(t) = \vec{H}(t) \cdot \vec{L}_i \rho_i, \tag{9}$$

where $\vec{L}_i$ is defined having the direction of the position of the i-th electrode (e.g., precordial electrode 1 to 6), and $\rho_i$ is an unknown normalization factor for each electrode. When normalizing the heart vector, the derived voltage is set approximately equal to the actual voltage recorded at the same lead:

$$Vd_i(t) \approx V_i(t) \tag{10}$$

The unknown factor $\rho_i$ for every lead can therefore be calculated as a minimum of the function:

$$F_i = \int_0^T \left[ V_i(t) - \vec{H}(t) \cdot \vec{L}_i \cdot \rho_i \right]^2 dt \tag{11}$$

where T is the recording time (e.g., 5 seconds). From this, we derive the relationship:

$$\rho_i = \frac{\int_0^T V_i(t) \cdot \left[ \vec{H}(t) \cdot \vec{L}_i \right] dt}{\int_0^T \left[ \vec{H}(t) \cdot \vec{L}_i \right]^2 dt} \tag{12}$$

Thus, we can calculate the lead normalization factors corresponding to each of the precordial electrodes (i=1 to 6). From all of these normalization factors, we can determine a common normalization factor, $\rho$. For example, the common normalization factor may be the average value of the individual normalization factors (e.g., when recorded from the six precordial leads):

$$\rho = \frac{\sum_{i=1}^{6} \rho_i}{6}. \tag{13}$$

Although equation (14) illustrates the normalization factor as an average of individual lead normalization factors, a normalization factor may be any value from the range defined by the lead normalization factors (e.g., the range defined by the maximum and minimum lead normalization factors). Furthermore, a normalization factor ($\rho$) for the heart vector may be any reasonable combination of lead normalization factors. For example, the normalization factor may be equal to the median of a plurality of lead normalization factors. Although example 2 shows the calculation of a normalization factor ($\rho$) from six precordial leads, a normalization factor may be calculated using only a single lead (e.g., $V_1$) or any combinations of leads (e.g., $V_2$, $V_3$, $V_4$), including non-standard leads. In particular, the normalization factor may be calculated using the leads (e.g., actual leads) comparable to leads used to derive (or used with) any criterion or benchmark applied by the ECG analyzer.

Furthermore, it should be apparent that the calculation of $\rho$ does not require the calculation of individual lead normalization factors, $\rho_i$. For example, a normalization factor may be calculated from the least-squares difference of the sums of the actual lead waveforms and the virtual lead waveforms, over some time, T.

Figure 11:
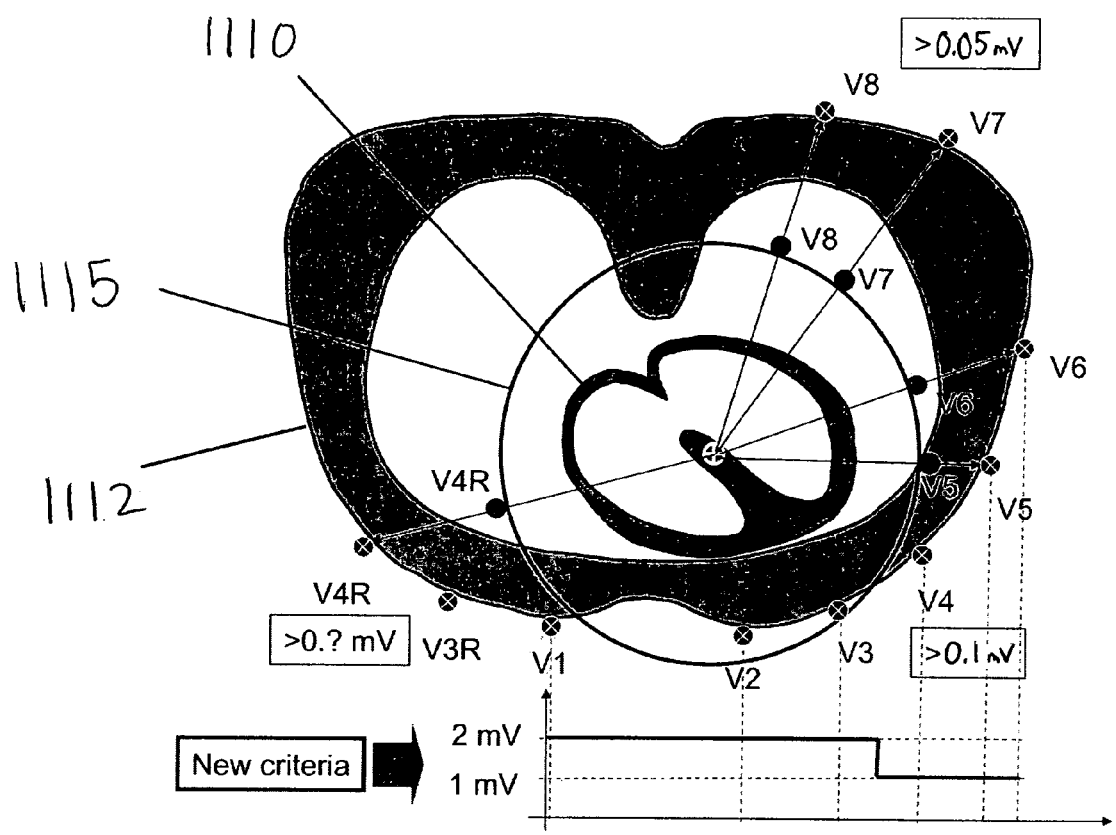
FIG. 11 shows an example of a normalized heart vector.

FIG. 11 shows an example illustrating normalization of the heart vector. The heart vector may be normalized to a virtual surface (sphere) 1115 surrounding the heart 1110 within the chest wall 1112. The radius of this normalization surface is calculated from the chest lead vectors ($V_1$, $V_2$, $V_3$, $V_4$, $V_5$, and $V_6$). The analogous leads on the virtual surface ("virtual leads") have the same directions, but different distances from the heart compared to real surface leads, since all virtual leads have the same distance from the heart defined by the average of conventional chest lead distances. As used here, "distance" may mean either physical distance or "electrical distance." Electrical distance corresponds to the electrical attenuation of the heart electrical signal measured on the body surface. In particular, when referring to the radius of the normalized virtual sphere, the radius is expressed as an electrical distance, in terms of attenuation. Thus, the radius of the virtual sphere does not correspond to any physical radius (e.g., position from the heart), but instead refers to the electrical distance from the heart.

FIG. 11 also shows the correlation of clinically relevant criterion used to analyze ECG data. One empirically based diagnostic benchmark used to detect acute ischemia is an ST segment shift of more than 0.1 mV in two or more adjacent leads from the chest. Thus, this criterion correlates well to chest leads (e.g., $V_1$, $V_2$, $V_3$, $V_4$, $V_5$, $V_6$). For leads V8 and V7, an ST segment shift of 0.05 mV may indicate ischemia. Another ST segment shift criterion that may indicate ischemia (shown as "new criterion" in FIG. 11) is an ST segment shift of more than 0.2 mV in the $V_1$, $V_2$, $V_3$ leads, or more than 0.1 mV in the $V_4$, $V_5$, $V_6$ leads. The normalization procedure described herein may allow the use of a single criterion to be applied to any virtual lead (e.g., chosen from anywhere around the heart). For example, when the six chest leads are used to normalize the heart vector, an arbitrary virtual lead from anywhere around the heart may be accurately compared to a criterion normally applied to the six chest leads (e.g., the 0.1 mV criterion) as if the virtual lead were one of the six chest leads.

The heart vector may be normalized by scaling the magnitude of the heart vector with the normalization factor, ρ:

$$\vec{H}_{NORMALIZED}(t) = \vec{H}(t) \cdot \rho \text{ or} \quad (14)$$

$$\vec{H}_{NORMALIZED}(t) = \rho(X\vec{i} + Y\vec{j} + Z\vec{k}) \quad (15)$$

where $\vec{H}_{NORMALIZED}(t)$ is the normalized heart vector. From the normalized heart vector, a normalized "virtual" ECG waveform can be calculated at an arbitrary point around the heart, as previously described:

$$V_1' = \rho(l_x*X + l_y*Y + l_z*Z) \quad (16)$$

where $V_1'$ is the normalized time-dependent electric potential at an arbitrary point on the patient's body, and $l_x$, $l_y$, $l_z$ are the components of a lead vector L for that arbitrary point on the body surface, and X, Y, and Z are the orthogonal components of the heart vector, and ρ is the normalization factor. The lead vector, L, may have a constant magnitude, defined by the module of the lead vectors used to calculate the normalization factor.

Normalization may allow comparison of cardiac voltage levels anywhere around the heart with clinical benchmarks (e.g., ST-segment shift), or with other regions of the heart. Normalization may be particularly helpful for ECG or other tests that rely, at least in part, on the magnitude of recorded cardiac electrical signals, such as ST segment shift, which is one of the most widely accepted diagnostic tests for ischemia.

While heart vectors may be able to provide information about cardiac electrical activity anywhere around the heart (e.g., away from the recording electrodes), and may be used to generate "virtual" ECG tracings, the magnitudes of these signals may not be adequately analyzed unless they are normalized as described herein. Normalizing the heart vector, and therefore any "virtual" ECG tracings generated from the normalized heart vector, may allow the magnitude of the cardiac electrical data from any virtual recording location around the heart to be compared with clinically proven criterion.

A normalization factor may be calculated for each individual patient ECG data set. Normalization factors may therefore be patient specific or patient ECG-data set specific. Preliminary results suggest that normalization factors calculated using the six precordial leads may be highly variable between patients, emphasizing the importance of normalizing for each set of patient data, so that the same criterion may be used to analyze patient heart data across patient populations.

Any of these cardiac electrical signals (e.g., heart vectors, normalized heart vectors, etc.) may be presented with a three-dimensional model of the heart that contains both temporal and spatial information about cardiac electrical activity, and may be coordinated with traditional ECG waveforms or the simulated and/or normalized signal waveforms. This displayed information may allow manipulation and further analysis of the cardiac electrical data.

C. Display of Cardiac Electrical Activity

Recorded and simulated cardiac data may be displayed and manipulated by the user in three-dimensional and two-dimensional representations. Cardiac electrical signals may be represented on a three-dimensional model of a heart; this model may be rotated by the user or automatically rotated. A user may select points on the heart for which cardiac electrical signals may be displayed. One or more ECG waveforms may also be displayed along with the three-dimensional model of the heart, e.g., as a two-dimensional plot of voltage over time.

Heart Model

Any suitable model of the heart (e.g., anatomical models) may be used as the heart model, including simulated heart models, and heart models based on actual patient data. In some versions, the heart model may be correlated to actual patient physiology. For example, the heart model may be derived from a medical scanning technique (e.g., CT, MRI, etc.) Thus, the heart model may reflect individual patient anatomy.

In some versions, the heart model may be entirely simulated. Such models may be based on actual patient data (e.g., a composite based on population information). A variety of heart models may be used. For example, classes or categories of heart models may be used that reflect a population that may be matched to the patient whose ECG data is being analyzed. For example, the ECG analyzer may choose which heart model to use based on information provided about the patient, including characteristics from the ECG data and additional information. Thus, there may be typical heart models for gender, weight, age, etc.

The heart model may also be a combination of patient data and simulation. The heart model may include features that reflect an individual patient's anatomy, medical condition, or medical history. For example, the heart model may be a simulated heart that contains markers indicating previous coronary events, scars, or surgical operations.

Presentation of Cardiac Data

FIG. 1 shows one example of a device for providing a three-dimensional presentation of ECG data. A patient 1 is connected to the electrodes and cables 2 for recording standard 12-lead ECG (leads I, II, III, aVR, aVF, aVL, V1, V2, V3, V4, V5 and V6). Data may be acquired by an acquisition module 3 that amplifies and A/D (analog/digital) converts the electrical signal. It may contain an amplifier level and an A/D converter. Thus, an acquisition module may function as a standard digital ECG device.

Figure 2:
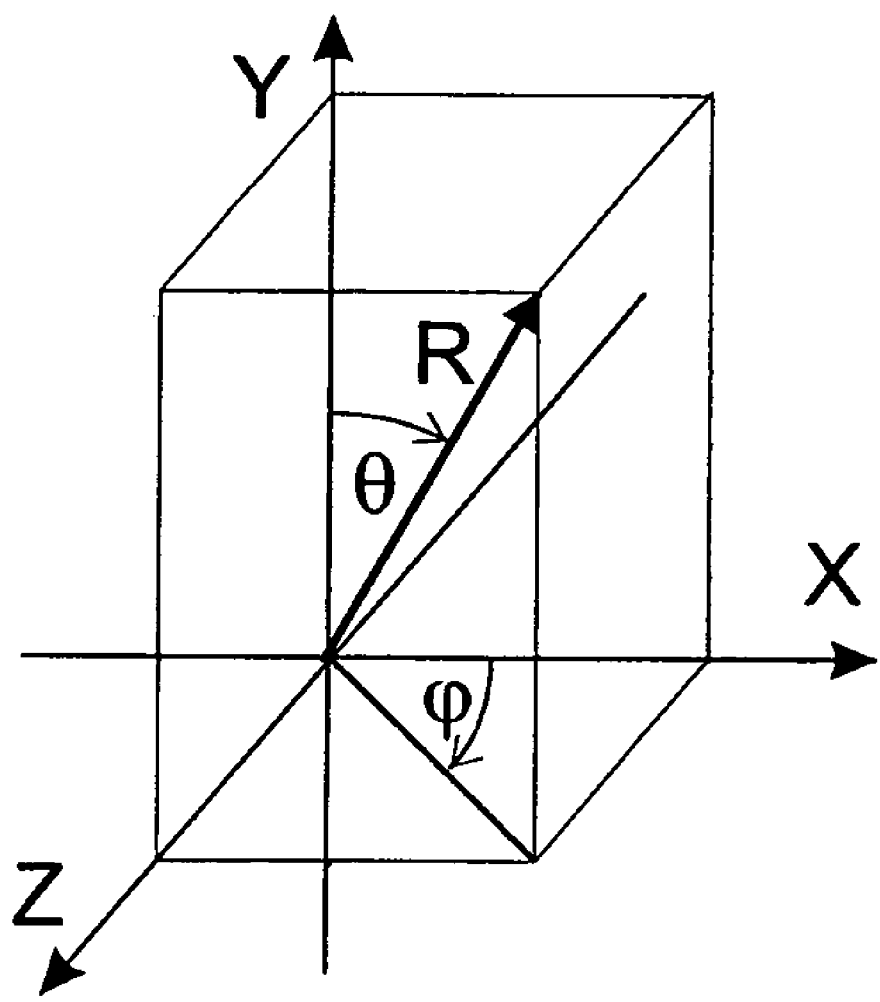
FIG. 2 shows the Frank orthogonal coordinate system.

In this example, signal processing module 4 filters, eliminates the base line fluctuation, and converts the standard 12 ECG leads into three orthogonal vector leads X,Y and Z. Frank vector leads are used for the derived X, Y, and Z leads, as described (Frank, E., An Accurate, Clinically Practical System For Spatial Vectorcardiography, *Circulation* 13: 737, May 1956). An orthogonal coordinate system with the axis orientation used for the Frank vector system is shown in FIG. 2. An inverse Dower's matrix is used for conversion of 12 leads into X, Y, and Z (Edenbrandt, L., Pahlm, O., Vectorcardiogram synthesized from a 12-lead ECG: superiority of the inverse Dower matrix, *J. Electrocardiol.* 1988 November; 21 (4):361-7). The three orthogonal leads X, Y, and Z may be obtained by other conversion matrices or other methods. For example, Kors (Kors, J. A. et al., Reconstruction of the Frank vectorcardiogram from standard electrocardiographic leads: diagnostic comparison of different methods, *Eur. Heart J.* 1990 December; 11(12):1083-92), Levkov (Levkov, C. L., Orthogonal electrocardiogram derived from the limb and chest electrodes of the conventional 12-lead system, *Med. Biol. Eng. Comput.* 1987, 25, 155-164), and the like.

In this example, an interactive visualization module 5 includes a processor 6, a monitor 7, input and output devices (a keyboard 8 and a mouse 9), and memory 10. The visualization module 5 uses signals X, Y, and Z from the signal processing module 4, enabling different ways of visualizing the electrical activity of the heart on the screen 7. Recorded signals, including personal and other diagnostic data of a patient, may be stored in digital form in databases in the memory 10 or used in data processing or display.

Figure 3:
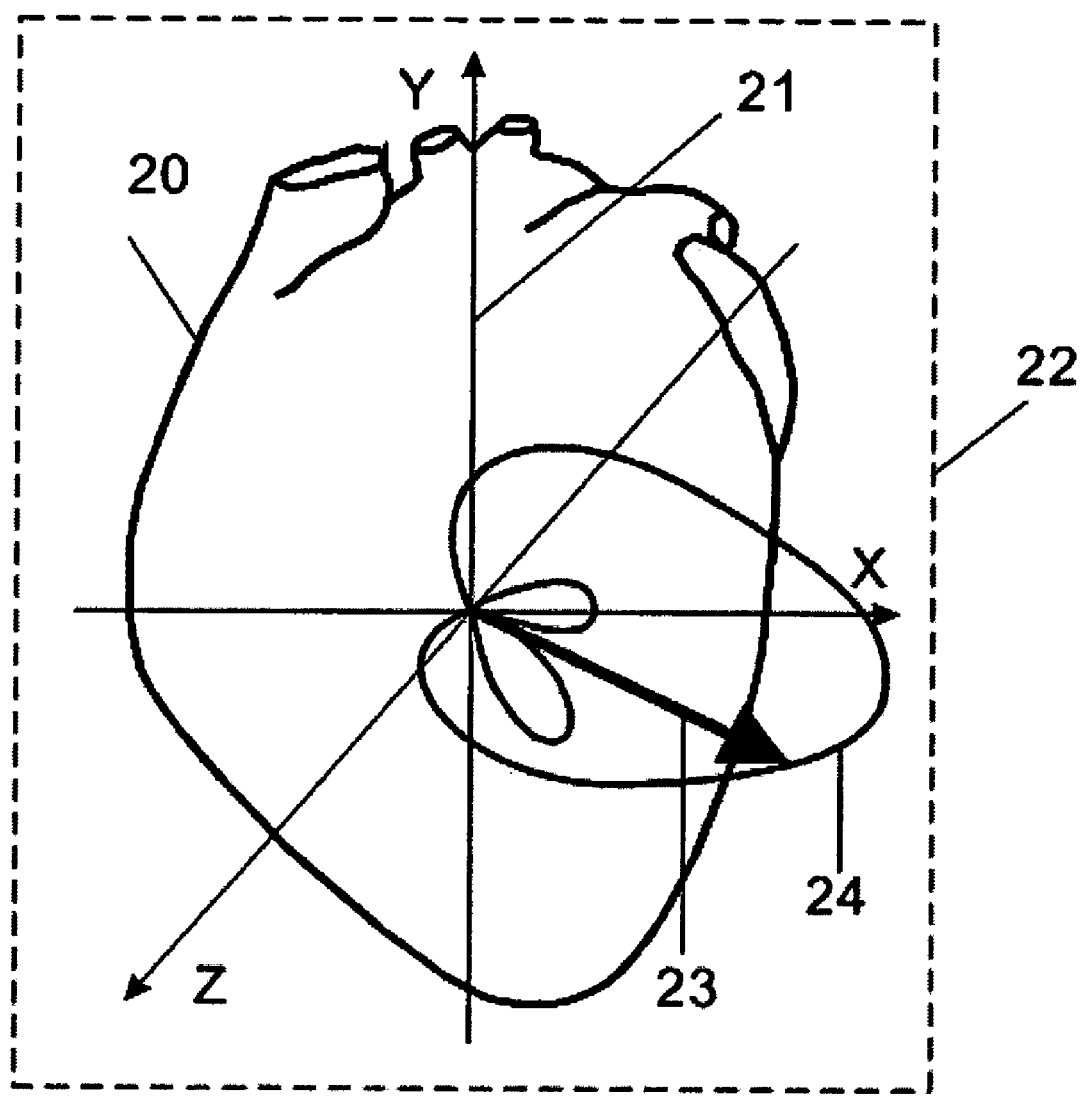
FIG. 3 shows a heart vector hodograph on a three-dimensional heart model.
Figure 4:
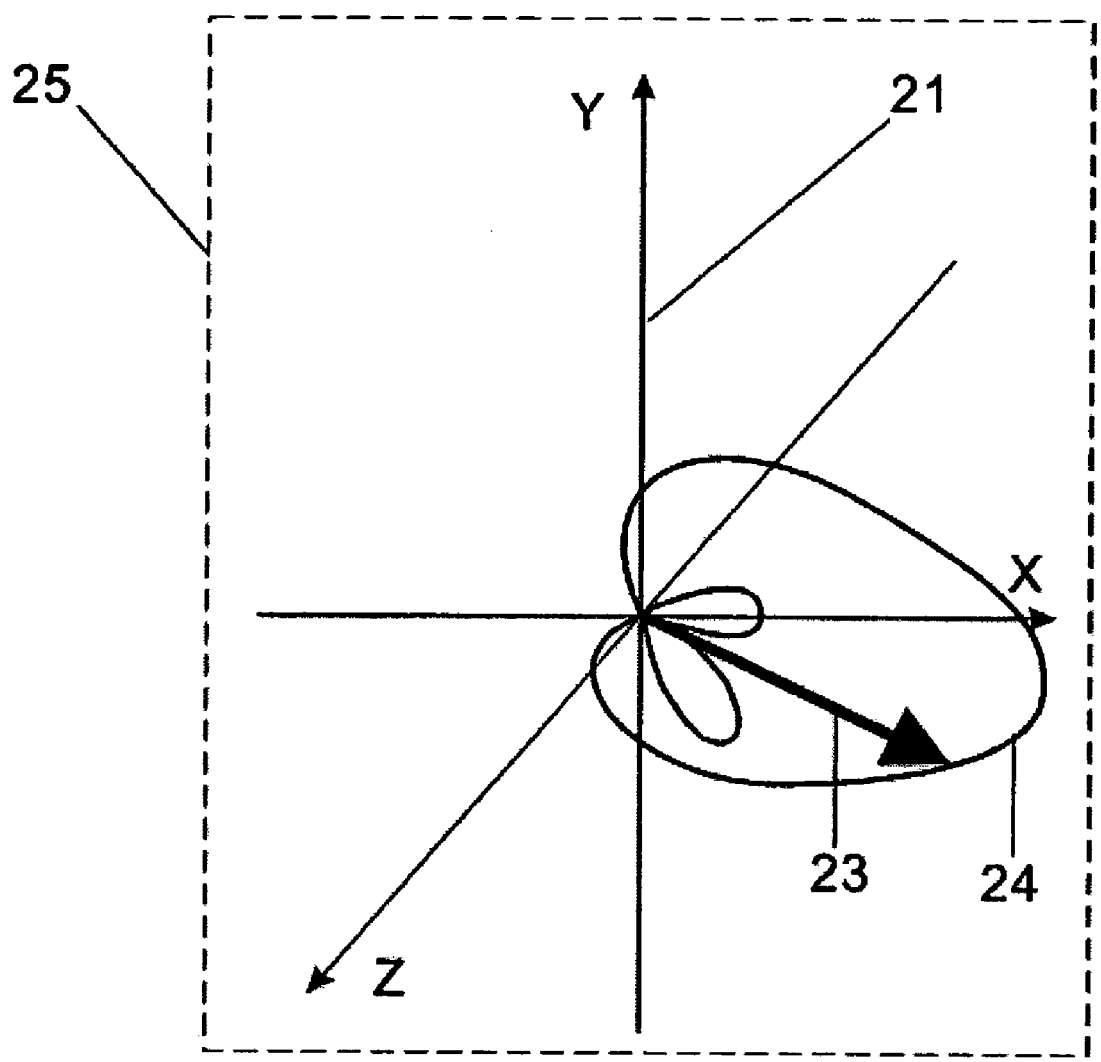
FIG. 4 shows an isolated hodograph of a heart vector.
Figure 5:
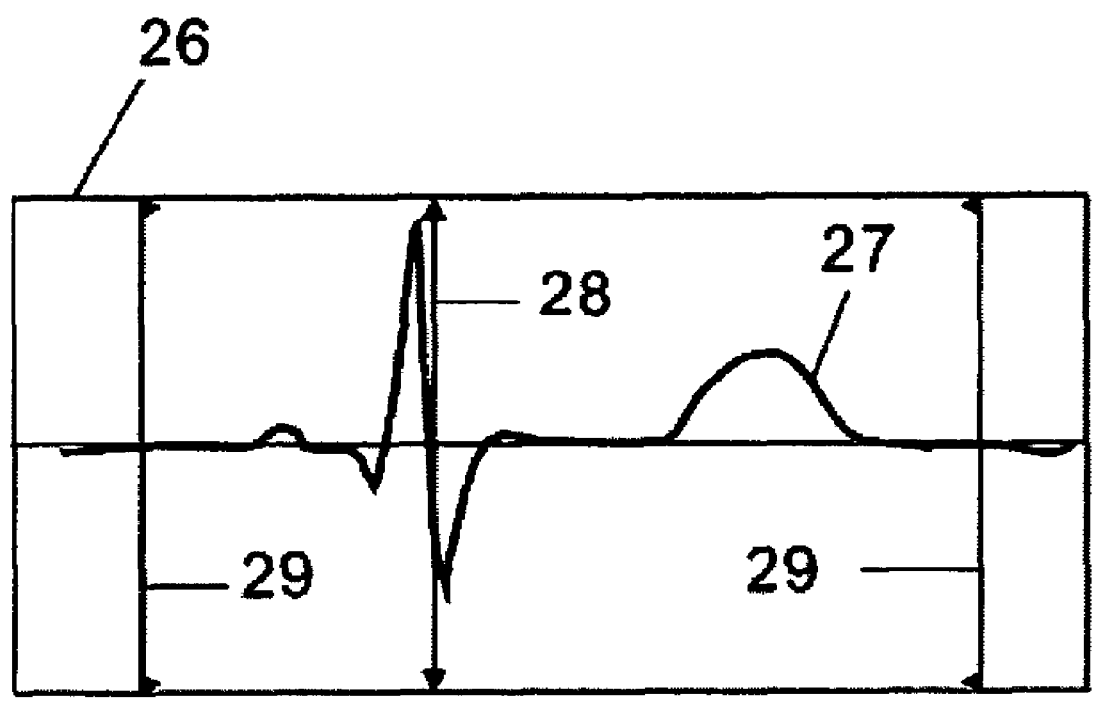
FIG. 5 shows an example of a waveform from one of 12 standard ECG leads.

The basic assumption enabling visualization of the electrical activity of the heart is that electrical activity can be approximated by an electric dipole. The electrical signal of the heart may be presented on a three-dimensional model of the heart 20, as shown in FIGS. 3, 4, and 5. The heart model can include basic anatomic elements, such as the aorta and other major blood vessels. Input and output devices (e.g., the keyboard 8 and the mouse 9) may be used for interactive manipulation of the model 20 and of the presented signals.

The model may be rotated. For example, the model may be interactively rotated around two orthogonal rotation axes (e.g., using the mouse 9), and it may be brought into any position on screen, meaning that any view of the heart and associated signal can be chosen by a user. The heart may be rotated around two imaginary rotation axes (which may not be shown on screen), such as the horizontal and vertical axes in the screen plane. A user may control the movement of the heart model through any appropriate input device (e.g., a keyboard or mouse). For example, by moving a mouse 9, the model may be rotated up-down and left-right. In some versions, the model heart is rotated automatically (e.g., it may center a particular feature such as electrical potential or cardiac abnormality, or it may continuously rotate about one or more axes).

As the model is rotated, any information displayed on the heart model may also be rotated. For example, the coordinate system for the model, the heart vector, and the lead vector may be rotated with the heart model. The coordinate system 21 is linked to the model, and may be shown as three orthogonal axes X, Y, and Z, which are rotated together with the rotation of the heart model, so that the model orientation regarding the patient's body is obvious at any view angle. An orientation guide, or body-referenced coordinate system, may also be included for indicating the orientation of the heart relative to a patient. For example, a small figure of a person may be displayed and oriented to show the heart orientation relative to a patient's body.

The heart model (or portions of the model) can be made transparent. For example, a user may select a command from the keyboard 8 or the mouse 9 to make a portion of the model transparent, revealing basic anatomic structures within the heart (e.g., atria and ventricles).

Visualization of analyzed ECG data may include: (1) graphical presentation of the heart vector hodograph, (2) graphical presentation of the signal waveform at an arbitrarily chosen point on the heart, and (3) graphical presentation of the map of equipotential lines on the heart at a chosen moment.

(1) Graphical Presentation of the Heart Vector Hodograph

Graphical presentation of the heart vector, and the heart vector hodograph, is shown in FIGS. 3, 4, and 5. When the heart vector hodograph is shown on screen, three elements may be visible: the first element 22 (FIG. 3) shows the heart vector 23 and its hodograph 24 on a three-dimensional heart model 20, i.e., it shows the path line of the top of the heart vector during a single heartbeat cycle; the second element 25 (FIG. 4) shows the hodograph 24 of the heart vector with the heart vector 23 and coordinate system 21 without displaying the heart model; the third element 26 (FIG. 5) gives a waveform 27 of one of the 12 standard ECG leads. The waveform may be selected from either an actual ECG waveform (e.g., from the data presented) or it may be a virtual waveform selected using the heart model. Waveforms from any of the 12 standard ECG leads, which may be presented as in element 26, may be chosen interactively. The heart model may also indicate the location of the lead from which the ECG waveform originated.

These three display elements may be correlated so that when a time or spatial point is selected from one display, the selection (or change) is reflected in the other displays. In FIGS. 3 and 4, the heart vector is shown by the arrow 23 at the same moment in time. The moment (e.g., the time value for this heart vector) is correlated to the position of the vertical marker line 28 in the ECG waveform in FIG. 5 (element 26). A user can select any time value. In some versions, the user may select a time value by interactively moving (or placing) a cursor 28 on an ECG waveform. In this way, a major drawback of vector ECG related to the loss of the time axis, i.e., the waveform, as mentioned earlier has been eliminated.

The user may also select the time interval to be displayed on the heart vector hodograph (e.g., the number of heart cycles or amount of a single heart cycle). In FIG. 5, element 26, showing the waveform, there are two vertical marker lines 29 (left and right) that can be moved interactively along the waveform, thus defining a time interval (between the two marker lines) shorter that a complete heartbeat cycle, making only the corresponding portion of hodograph visible. In FIG. 5, the brackets 29 show that a complete cardiac cycle (PQRST) have been selected, and are displayed as a cardiac hodograph in FIGS. 3 and 4. In some versions, the user selects the time period of interest. For example, the user may interactively move the brackets 29. When multiple cycles are selected, the hodograph may be computed by processing the data from different cycles so that a single (e.g., averaged or subtracted) hodograph is shown.

The heart model and visualized electrical activity may be moved interactively, and rotation of the different components (e.g., the 3D and 2D elements) may be synchronized. For example, the common axes of the coordinate systems 21 may be kept parallel at any view angle. The same applies to the presentation of the heart vector 23 in the elements 22 and 25.

Figure 12:
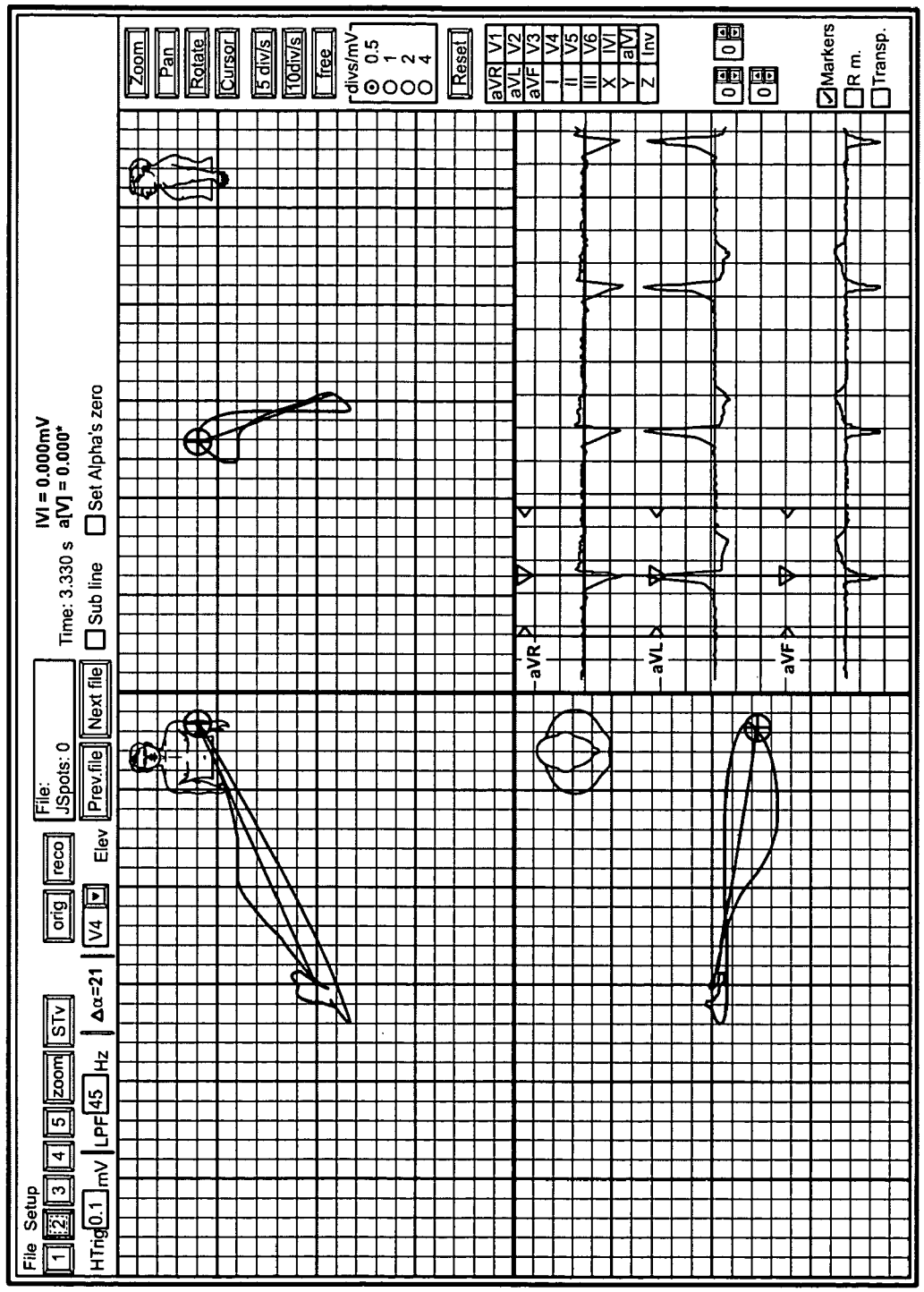
FIG. 12 shows an example of a hodograph tool using the ECG Analyzer as described herein.
Figure 13:
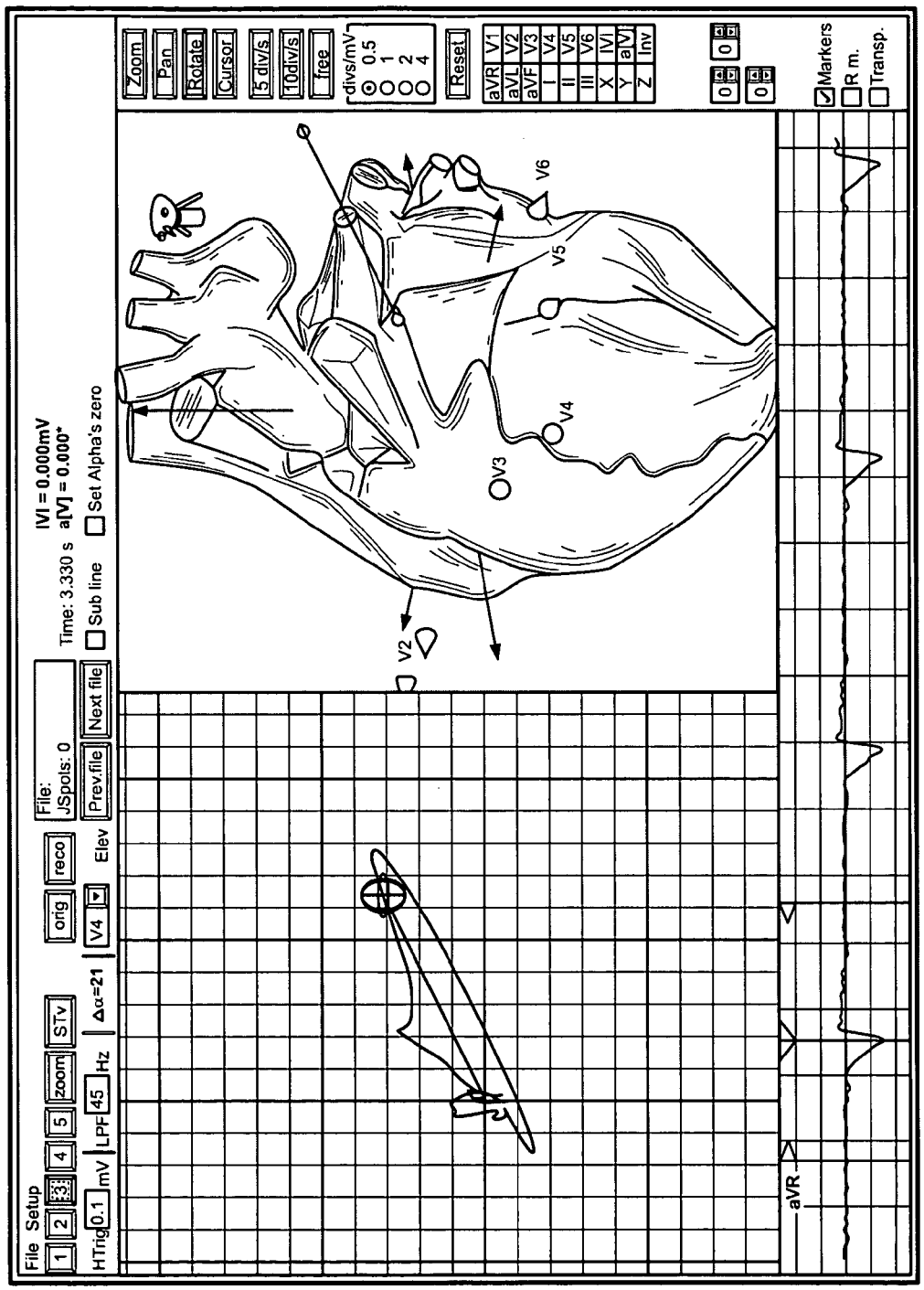
FIG. 13 shows another example of a hodograph tool using the ECG Analyzer as described herein.

FIGS. 12 and 13 show examples of images that may be displayed by the ECG analyzer. FIG. 12 shows three conventional vectorcardiographic presentations (e.g., three 2D vector hodograph loops, in three orthogonal planes: frontal, sagittal, and horizontal) in which heart vector is shown in individual plane, together with a tool for selection of the time instant corresponding to the heart vector using ECG waveforms, shown in the bottom right corner. FIG. 13 shows a 3D vector hodograph loop presentation, including the heart vector and a 3D representation of the heart vector (white arrow) on a heart model (the chest lead are shown projected on an imaginary sphere surrounding the heart model). FIG. 13 also shows a tool for selection of the time instant corresponding to the heart vector from ECG waveforms on the bottom of the screen.

Figure 6:
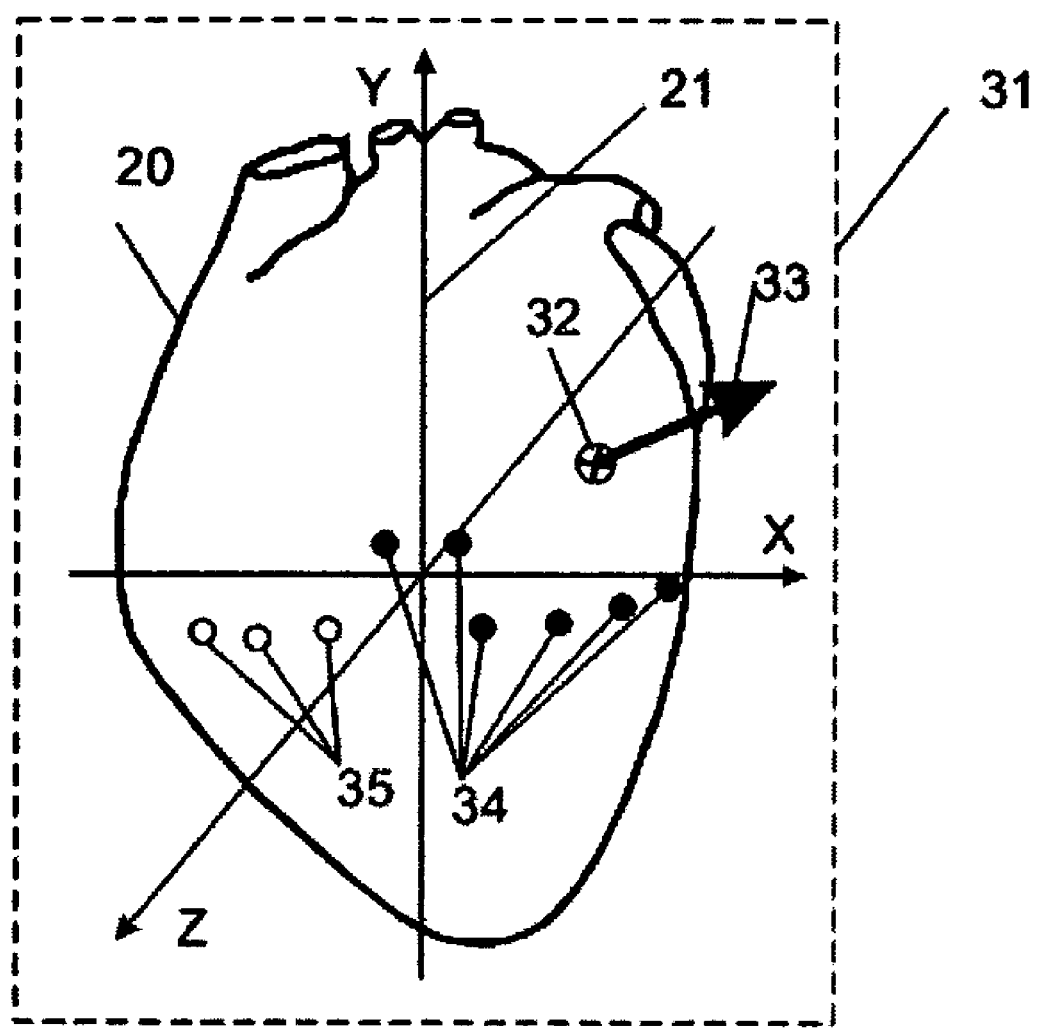
FIG. 6 shows a heart model on which an arbitrarily chosen point has been selected.

(2) Graphical Presentation of the Signal Waveform for an Arbitrarily Chosen Lead on the Heart A "virtual" lead may be calculated using the normalized heart vector for any point on the surface of a heart model. The point may be selected by the user. In some versions, the user may select any point on the continuous surface of the heart model. In some versions, regions of the heart model may not be selectable (e.g., regions that are not electrically active). An example of the graphical presentation of a signal waveform for an arbitrarily chosen point on the heart is given in FIGS. 6, 7, and 8. All of these elements, or a subset of these elements, may be displayed, so that a user may see a 3D heart model, an actual ECG waveform, and/or a virtual ECG waveform.

The first element 31 (FIG. 6) shows a heart model 20 that includes a symbol 32, depicted as a small circle, defining the position of an arbitrarily chosen lead. The symbol 33 presents a lead vector perpendicular to the heart model surface at the position of the arbitrary lead attached to the symbol 32. The symbols 34, that correspond to the positions of the standard ECG leads (V1, V2, V3, V4, V5 and V6), and 35, that correspond to the positions of the special ECG leads (V7, V8, V9, V3R, V4R and V5R), are also shown. Any point of interest may be indicated on the heart model, including the location of leads (actual and virtual).

The second element 36 (FIG. 7) shows a waveform of one of 12 standard ECG leads as previously described for FIG. 5, but without the marker lines 28 and 29. In all of the images of ECG waveforms, the time axis may be shown, and may be labeled.

The third element 38 (FIG. 8) shows a "virtual" signal waveform 39 determined at an arbitrarily chosen point on the heart, by selecting a point using the heart model. This signal waveform 39 may be determined based on the position of the symbol 32 on the heart surface. As mentioned, a user may interactively and continuously move the symbol 32 across the surface of the heart model 20. Moving the symbol may change the waveform 39 shape so that it corresponds to the waveform for the position of the symbol 32 on the surface of the heart. In one version, as the user moves the symbol across the surface of the heart model, the ECG waveform updates and reflects the continuous change in the waveform as position changes.

The correlation between the ECG waveform 39 and the position of the symbol 32 on the heart may be calculated using the heart vector and the normalizing lead vector, as described above. Thus, the electric potential V1 in an arbitrary point on the patient's body, i.e., the value of the recorded lead signal, is given by the scalar multiplication:

$$V_1 = l_x * X' + l_y * Y' + l_z * Z' \qquad (17)$$

where $l_x$, $l_y$, $l_z$ are the components of the lead vector L of an arbitrary point on the body surface, and X', Y', and Z' are the components of the normalized heart vector, i.e., the values in three orthogonal vector leads as they have been defined earlier. The values of the lead vector L at points that correspond to standard ECG leads are used to obtain orthogonal leads X, Y, and Z. By using the equation (1), one can obtain the potential $V_1$, i.e., the corresponding waveform on the basis of the orthogonal leads for the known value of vector L for each standard measurement point, using the normalizing lead vector. The resulting values are normalized. On the basis of this concept, one can obtain values $V_1$ for any other point, provided that the value of the vector L that corresponds to the position of the point is known. The waveform 39 is obtained using the equation (1) so that for values of the lead vector L that correspond to the position 32 the angle coordinates of the point 32 are used. In this example, the vector module of the lead vector is set to the average value of the vector L module for precordial leads V1 to V6. This means that waveform 39 corresponds to virtual measurement points that would be positioned on a sphere having the same center as the heart model, with the radius corresponding to the average value of the radii of the precordial electrode measurement points (measured as an electrical distance, e.g., attenuation).

By interactively moving the symbol 32 on the heart model, a point on the surface may be chosen using the angle coordinates (oriented as presented in FIG. 2) corresponding to the measurement point on the virtual surface described by the lead vector (e.g., in this example, a sphere). The symbol 33 of the vector perpendicular to the heart model surface at an arbitrary lead position, which may move together with the symbol 32, shows a direction perpendicular to the heart surface and enables better visual information on the exact angular position (with respect to heart orientation) of the chosen measurement point marked by the symbol 32.

In some versions, points or data (e.g., equipotential plots) selected or indicated on the heart model surface may be projections onto the heart model surface from an imaginary surface (e.g., a sphere) around the heart model. Thus, points may be selected from the imaginary spherical surface and shown (e.g., by orthogonal projection from the imaginary sphere) on the heart model, simplifying the display and processing using an irregularly shaped heart model.

Figure 7:
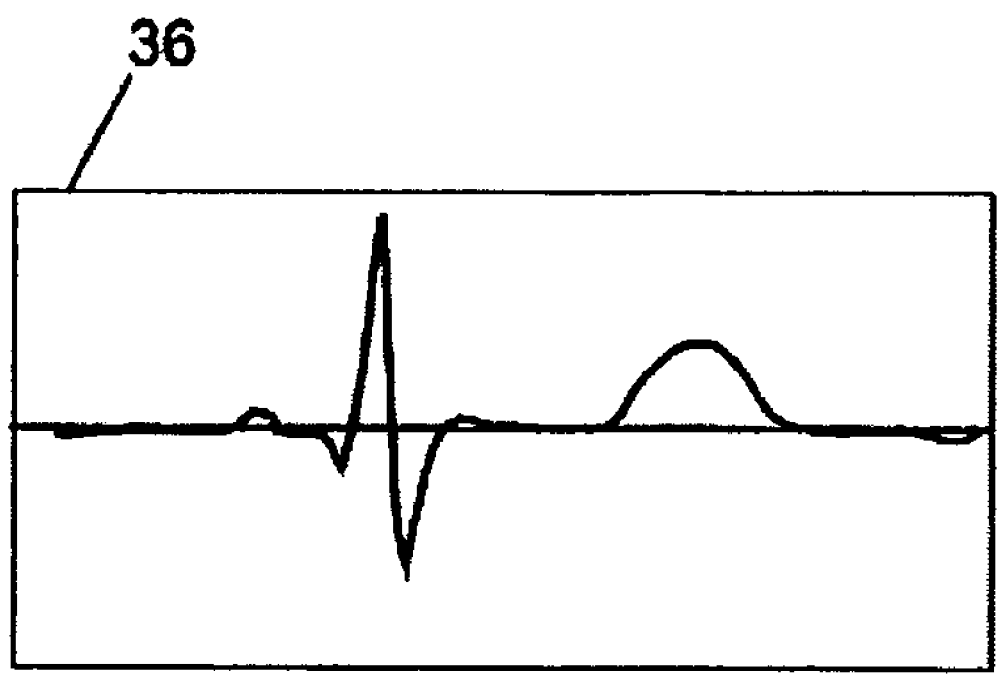
FIG. 7 shows an example of an ECG waveform from one of 12 standard ECG leads.
Figure 8:
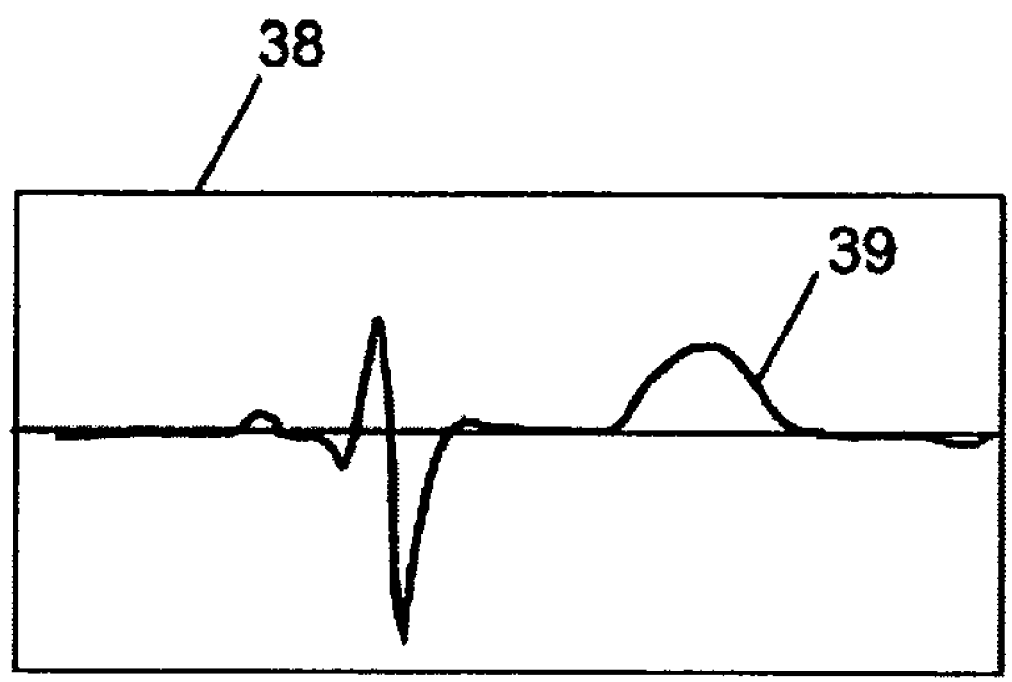
FIG. 8 shows an example of a signal waveform derived from an arbitrarily chosen point on a heart model.

The actual waveform (e.g., FIG. 7, the second element 36) and the virtual waveform (e.g., FIG. 8, the third element 38) may also be directly compared. For example, these waveforms may be drawn adjacent to each other, or they may be placed on the same graph (e.g., displayed in different colors or patterns). A "subtracted" waveform may also be generated, to highlight differences between the two (or possibly more) waveforms. Although FIGS. 7 and 8 show actual and virtual waveforms, any two waveforms may be displayed or compared. In some versions, more than two waveforms may be displayed and/or compared.

In any of the visual elements described herein, the user may magnify or "zoom" in or out of the image. For example, the user may zoom in on a region of the heart model, or a region of the ECG signal waveform. For example, the user may zoom out of an image of an actual or virtual waveform so that the time axis shows multiple PQRST waveform cycles; a single region in the time axis (e.g., corresponding to a single PQRST wave) may then be selected, zooming in on the image. When multiple waveforms are displayed, changing the scale of the time axis of one waveform may concurrently change the time axis on all of the waveforms displayed, or each waveform may have a different time axis scale. In some versions, the user may "scroll" through the time axis of one or more waveforms. The voltage axis of the ECG signal waveforms may similarly be controllable by the user and coordinated between the different waveform images.

In the 3D heart model show in element 31, symbols 34 that correspond to the angle coordinates of the standard ECG leads (V1, V2, V3, V4, V5 and V6) are also shown projecting onto the heart model. It can be seen from the previous explanation that if the symbol 32 is brought into the position of one of the symbols 34 (e.g., V6), and if the same lead (V6) is chosen on the heart model in the element 36, then the virtual signal waveform 39 in element 38 will have the same general shape as the actual ECG waveform of the V6 lead shown in the element 36. The signal amplitudes may differ by a factor dependent on the normalization. In this example, when the heart vector is normalized (e.g., to a sphere having a radius based on the average value of the precordial leads), the signal waveforms will differ by a ratio of the vector L module for the V6 lead in respect to the average value of module for precordial electrodes. In the 3D heart model shown in element 31, symbols 35 corresponding to the angle coordinates of the "special" ECG leads (V7, V8, V9, V3R, V4R and V5R), that are typically recorded only in special cases. The waveforms obtained by placing the symbol 32 onto these points may not be very similar to the corresponding recorded leads (as with the precordial leads), because the heart vector has been normalized.

Figure 14:
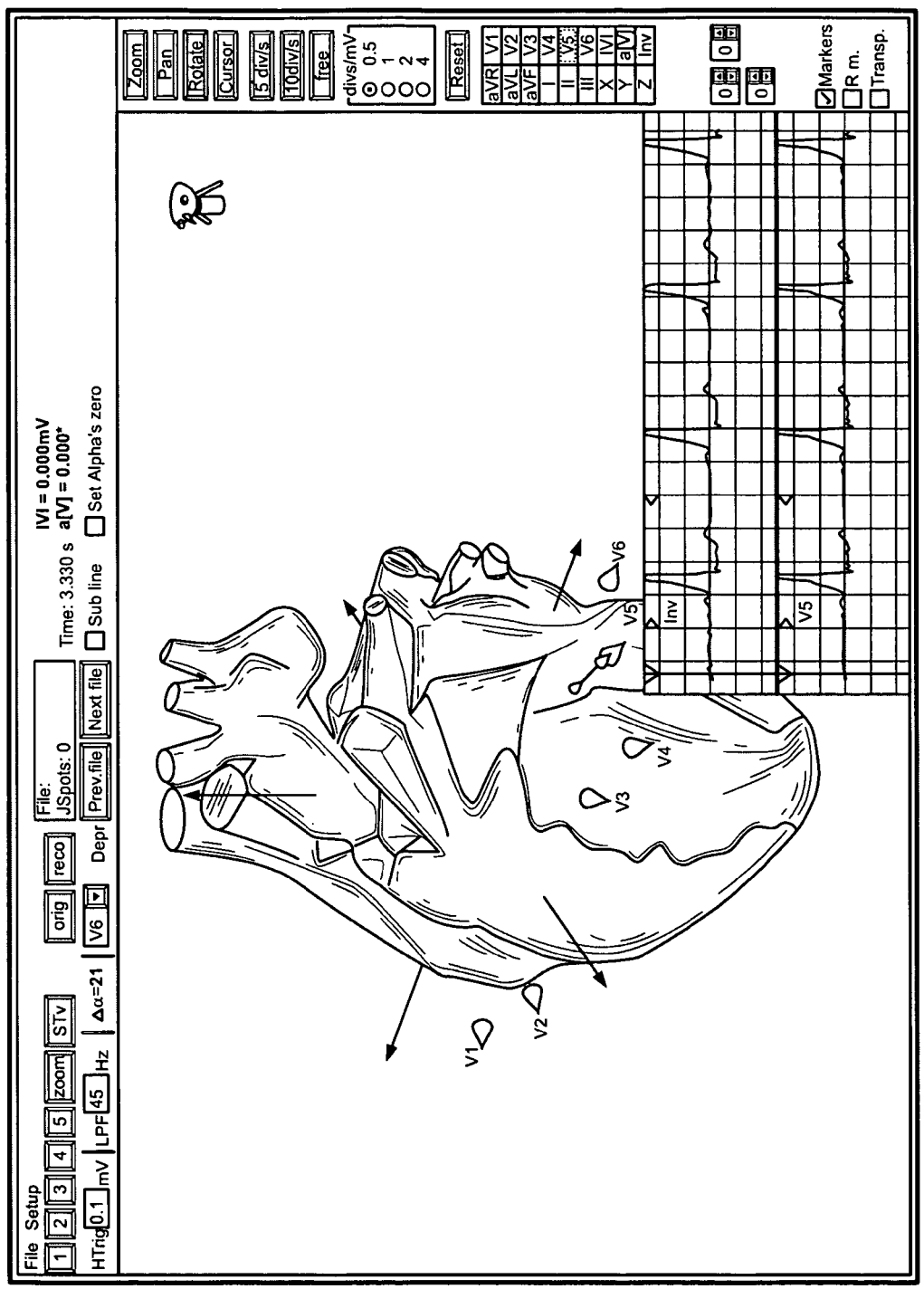
FIG. 14 shows an example of a virtual lead calculation tool using the ECG Analyzer as described herein.

FIG. 14 shows an example of a "virtual" signal waveform (labeled "Inv" in the bottom right) calculated from a virtual electrode at a selected point on the heart model (the selected point is represented by the white arrow). An actual signal waveform recorded on an actual recording point is also indicated (V5). In this example, the selected point corresponds to the real recording point, thus, the two waveforms have only small difference in shapes.

The normalized "virtual lead" measurement provides very useful diagnostic information, as described further below.

Figure 9:
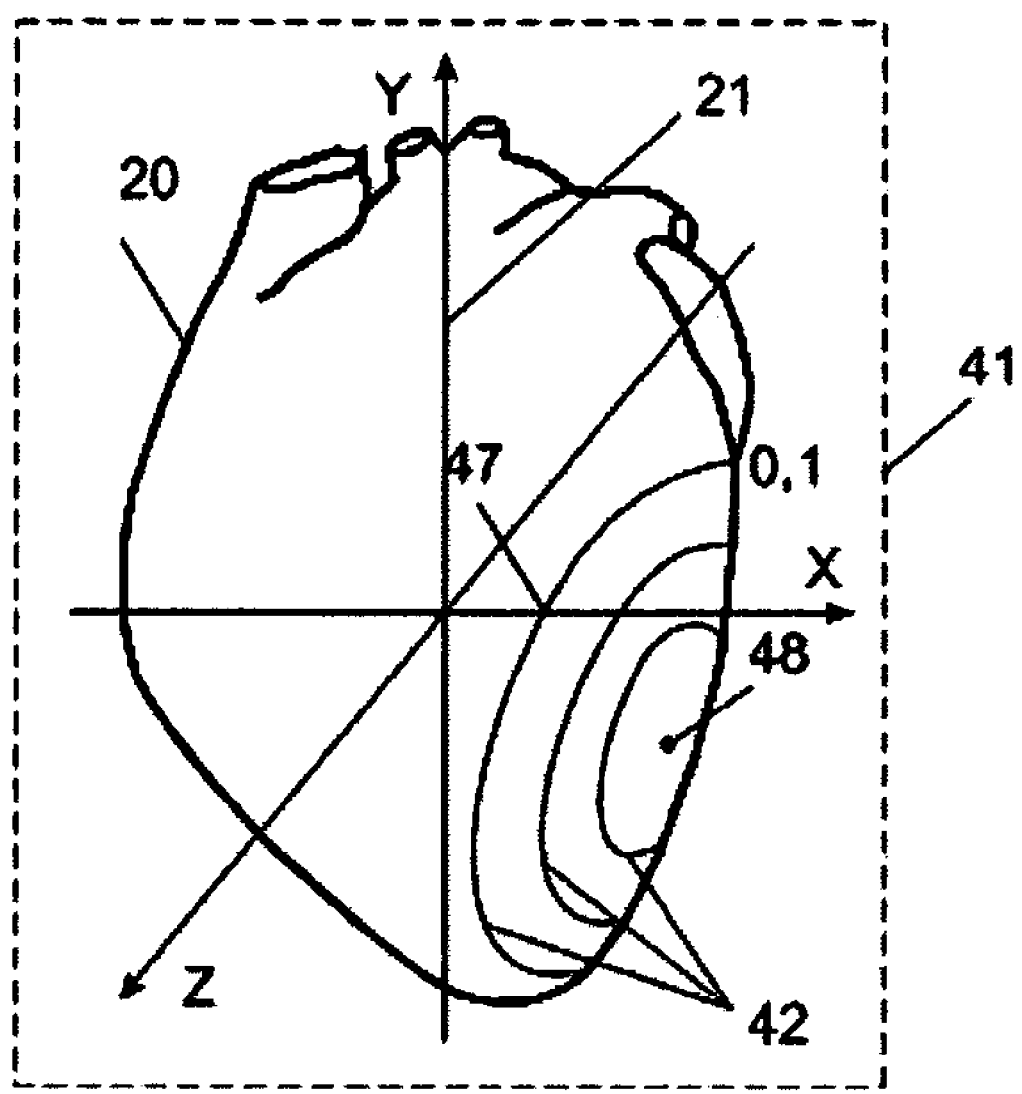
FIG. 9 shows a map of equipotential lines on a heart model at a chosen moment.
Figure 10:
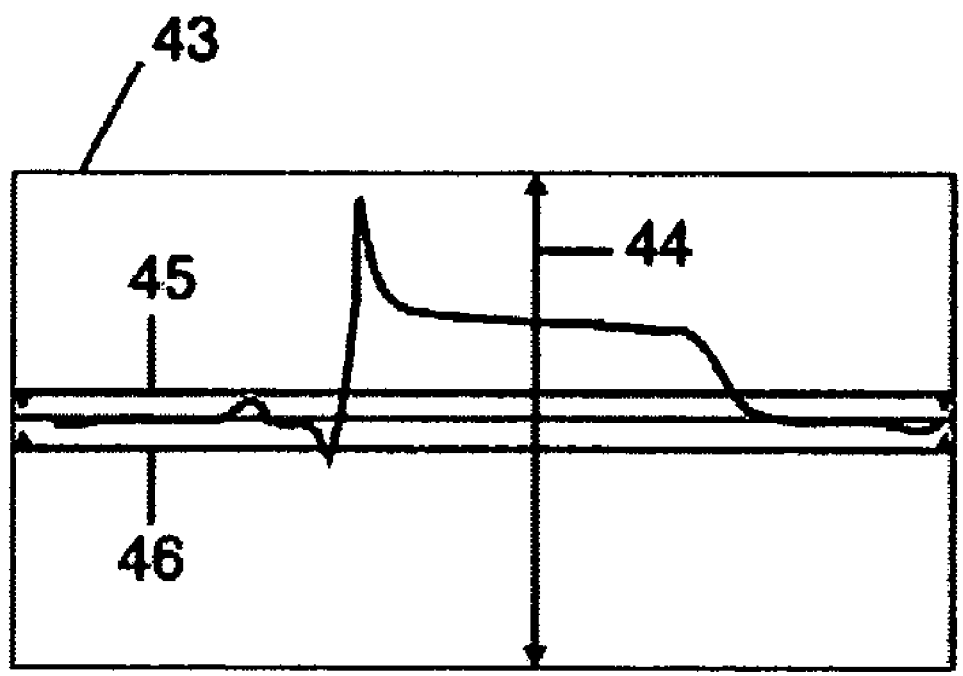
FIG. 10 shows an ECG waveform with marker lines.

(3) Graphical Presentation of the Map of Equipotential Lines on the Heart in the Chosen Moment A voltage map of the heart surface may be calculated at any time point, and displayed on the surface of the heart model. Equipotential lines are lines that connect all points having the same electrical potential (they may also be referred to as isoelectric or isopotential lines). Graphical presentation of a map of equipotential lines is shown in FIGS. 9 and 10. When this presentation is on screen, one may see two elements: the first element 41 (FIG. 9) shows a heart model 20 in which the map of equipotential lines 42 is shown for a chosen moment; the second element 43 (FIG. 10) shows an ECG waveform. In FIG. 10, the ECG waveform is shown as one of the 12 standard ECG leads.

As in FIG. 5, the ECG waveform includes a marker line 44 for choosing the moment (e.g., a time point) on the time axis. This time point may correspond to the displayed map 42 on the heart model. The ECG waveform may also include additional marker lines 45 and 46 for choosing a minimal potential (e.g., voltage) value, or a voltage range, for showing the equipotential lines.

Isopotential lines may be calculated from the normalized heart vector at any time, t, selected. The heart vector at the time point, t, will determine the center of the equipotential lines. A voltage step (ΔV) between adjacent equipotential lines (e.g., 0.05 mV, 0.1 mV, etc) may be selected or pre-set. Concentric equipotential lines may be separated by this voltage step. Isopotential lines may be determined using the normalized heart vector by calculating the derived ECG signal. The relationship:

$$Vd_i(t)=C_i, (i=1, \ldots n), \tag{18}$$

where $Vd_i(t)$ is the derived potential, t is the selected time, and Ci are predefined voltages, where $C_1$ is the minimal voltage selected (the threshold value), and each increasing voltage increases by the voltage step (ΔV). If a maximum voltage range is selected, $C_n$ may approximately equal the maximum.

Equipotential lines 42 shown on the heart model in element 41 are determined at the chosen time point that corresponds to the position of the marker line 44. These lines may be calculated on the basis of the normalized heart vector components as described above. The user may select a minimum absolute voltage value by choosing the position of the marker lines 45, 46, or a pre-set minimum voltage value may be used. This voltage determines a threshold so that cardiac electrical signals that fall below the absolute value of the threshold are not shown. For example, signal values between these marker lines will not be shown as equipotential lines on the heart model.

In general, information may be shown on the heart model by any appropriate method. For example, a transformation may be used to determine the position of a voltage (e.g., a normalized voltage) calculated from the heart vector that corresponds to the surface of the heart model. In one version, information is orthogonally projected on the heart model from an imaginary surface (e.g., a sphere) surrounding the heart. Typically, the center of the heart model is concurrent with the origin of the heart vector. The heart vector is a simplified dipole model with the center of the heart as the approximate origin of the dipole. Thus, cardiac electrical data calculated from the heart vector may be projected (orthogonally) onto the surface of the heart model. For example, equipotential lines may be calculated from the normalized heart vector as described above. This calculation method results in voltages which may be on the surface of an imaginary sphere surrounding the heart model (e.g., by scalar multiplication of the normalized heart vector to a lead vector). However, the voltage may be projected from the imaginary sphere surrounding the heart vector onto the heart model by orthogonal projection. Alternatively, a transformation reflecting the spatial relationship between the heart model and the body surface may be used to map the equipotential lines onto the surface of the heart model.

The technique of showing equipotential lines may also be used to indicate clinically relevant information, such as ischemia. For example, a time point (or time range) may be selected in the ST segment of the waveform, as shown by the marker line 44 in FIG. 10, and a minimum voltage level may also be selected (e.g., using marker line 45). Based on clinical data, when the minimum voltage of the ST segment exceeds 0.1 mV, the ST segment may be "elevated," indicating ischemia. This is described more fully below.

The choice of the position of all three marker lines, as well as rotation of the heart model 20, may be performed interactively so that the three-dimensional (heart model) and the two-dimensional (waveform) elements are correlated in time and space.

The map of electric potentials shown by equipotential lines may be shown in color. Furthermore, any of the display elements may be shown in color, and relevant values (e.g., magnitude, direction or time) may be indicated in color.

The interactive display may be part of an ECG analyzer. For example, the ECG analyzer may include modules 3, 4, and 5 (in FIG. 1) as components of a single device. Thus, the ECG analyzer may receive ECG data, process the data, display the data, and respond to user commands. In some versions, the ECG analyzer includes a computer having components such as a monitor or other display device, and one or more command inputs (e.g., from a keyboard or mouse). In some versions, the ECG analyzer includes a computer running software supporting the described procedure of data processing and/or interactive visualization. Additional output devices (e.g., printers, electronic connections, digital storage media, etc.) may be used, for example, for reporting output or printing chosen screen shots obtained during the process of visualization.

An ECG analyzer may include a display (e.g., as part of a display module) or it may present data in a format that may be displayed by an additional device. In some versions, the ECG analyzer does not prepare the processed cardiac data for display, but provides the processed (e.g., normalized) data for storage, or for use by other devices or methods. For example, the ECG analyzer may process ECG data, normalize the ECG data, and present this ECG data to another device or tool. The normalized ECG data may be digital data, vectors, or waveforms, or as any other useful format.

In some versions, the ECG analyzer does not provide graphical output. For example, the ECG analyzer may provide output, such as diagnostic information or analysis of patient ECG data, in non-graphical formats. The ECG analyzer may indicate the risk of a cardiac problem or electrophysiological state without displaying the analyzed data. Output may be text, tonal (e.g., "beeps" or other audible output), electronic (e.g., output to an electronic device), visual (e.g., toggling an indicator light), or the like.

D. Analysis Tools

Normalized cardiac electrical activity from the heart (e.g., the normalized heart vector) may be analyzed by any appropriate method. In particular, analysis tools may examine cardiac electrical activity processed as described above. Analysis tools may include tools for detecting abnormal or pathologic heart activity (e.g., ischemia), or for characterizing normal heart activity. The devices, systems, articles of manufacture, and methods descried herein may provide more accurate and clinically relevant information, because the ECG data is processed and normalized in a way that that allows the meaningful comparison of electrical activity recorded (or "virtually recorded") from anywhere around the heart.

ST Segment Analysis

Analysis of standard ECG is central to the physician's likelihood and risk estimates for cardiac patients, and may significantly affect subsequent therapeutic decisions (American College of Cardiology/American Heart Association Guidelines for the Management of Patients with ST-Elevation Myocardial Infarction, www.acc.org/guidelines/stemi/index.pdf, accessed 01-14-05). One of the principal techniques employed to interpret ECG data is the analysis of ST segment deviations and T-wave abnormalities.

For example, ST deviations may be used to predict the likelihood that a patient's symptoms are due to myocardial ischemia. This is particularly true if the changes are new or transient. ST segment and T-wave changes also contribute significantly to risk assessment. Patients with extensive changes in their ST segment (e.g., elevation or depression) are generally at higher short-term risk of death than patients with no or minimal changes (ACC/AHA 2002 Guideline Update for Management of Patients with Unstable Angina and Non-ST-Segment Elevation Myocardial Infarction, J Am Coll Cardiol 2002; 40:366-74).

The presence or absence of ST elevation may also determine a therapeutic pathway. Patients with ST-segment elevation myocardial infarction (STEMI) are generally treated with thrombolytic therapy or immediate coronary intervention (PCI, formerly termed balloon angioplasty), whereas patients with non-ST-segment elevation myocardial infarction (NSTEMI) or unstable angina are treated with medical therapy or PCI, but not thrombolytics.

Although information regarding ST segments is of critical importance in assessing patients with myocardial ischemia, standard 12-lead ECG techniques may underemphasize or completely fail to detect such events. Processing of the ECG data with the ECG analyzer may result in processed ECG data which is much more amenable to analysis of clinical indicators such as ST deviation.

Normalized ST-Segment Vector Magnitude

The ECG analyzer may be used to calculate a normalized ST-Segment Vector Magnitude (NSTVM) value calculated from the normalized heart vector. When the heart vector is normalized as described herein, an NSTVM value may be calculated at a point during the ST-segment (e.g., the J, J+60, J+80 point, etc.). NSTVM may be calculated using the formula:

$$NSTVM = \sqrt{X^2 + Y^2 + Z^2} \quad (19)$$

Where X, Y, and Z are the values for the magnitude of the normalized heart vector at the time point used (e.g., J+80). This value corresponds to the ST shift value in milivolts recorded if there was a lead (e.g., a precordial lead) directly over the center of the ischemic region. Thus, the NSTVM value is the ST shift value at some imaginary lead that would be just over the center of the ischemic region. After calculating the NSTVM value, this value may be compared to a threshold value that is a criterion for determining ischemia. When the heart vector is normalized to a value between the maximum and minimum values of the six precordial leads (e.g., the average of the modulus for the six precordial leads), The NSTVM value of grater than 0.1 mV may correlate to a positive inference of ischemia. This criterion (0.1 mV) may be derived from empirical data determined by interpreting standard EGC data, and has been recognized as a suitable criterion indicating ischemia. It should be obvious, however, that other NSTVM criterion may be used, including other empirically relevant criterion (e.g., 0.05, 0.1, 0.15 mV, 0.2 mV, etc.).

The classical "two leads greater than 0.1 mV" criterion is well established as a criterion indicating ischemia for the LAD (Left Anterior Descending) zone, and for the precordial leads. Thus, the NSTVM criterion (0.1 mV) is a generalization of the classical criterion. It is independent on the ischemia zone, and it will work for any heart zone in the same way that the traditional 0.1 mV criterion works for the precordial zone. Any appropriate criterion may be used. For example, a more precise criterion may be determined by empirically examining the normalized ECG data (e.g., the normalized heart vector or NSTVM) and clinical data.

The magnitude of an un-normalized heart vector may not be reliably compared to a single criterion value (e.g., 0.1 mV), and may not correspond to existing empirically-proven criterion. The normalization step may scale the magnitude of the heart vector so that it may be reliably compared with a criterion such as the greater than 0.1 mV criterion for ischemia. In some versions of the ECG analyzer, the heart vector is normalized to the mean value of chest ECG leads (the precordial leads). Thus, the heart vector may be normalized to a sphere centered in the center of the heart, having a radius that corresponds to the mean attenuation of the precordial leads from the heart. When the heart vector is normalized this way, the NSTVM level may be equivalent to the level of an ST shift that is centered under the V4 lead. The NSTVM may then be readily compared to the classical criterion for ischemia locations in the precordial zone. Thus, the normalized heart vector may be generalized to predict ischemia using the NSTVM for any other region of the heart. Normalizing the heart vector in this fashion may allow the NSTVM criterion to be equivalent to the ST-shift values criterion for chest leads and infarctions of the front wall, which are well established.

Evidence from electrocardiographic body surface mapping studies has indicated that the locations of leads sensitive for acute ischemia would optimally be placed largely away from the locations of conventional 12-lead ECG recording sites. Furthermore, the ST shift levels of limb and precordial leads are not equivalent, because the electrical conductivity of the body tissue between the voltage source (the heart) and the skin (i.e., attenuation) is not equivalent. For example, the lead vector magnitudes of leads V1 and V6 are in the same range. As a result, many clinicians and researches have suggested using ST criteria with different criterion voltage levels for different leads. The normalization performed by the ECG analyzer may eliminate the effect of different attenuation, allowing a single criterion for reliably identifying ischemia.

The NSTVM calculation may be part of an NSTVM tool, or a part of another tool, such as a visual Ischemia Monitoring tool.

Ischemia Monitor Tool

In practice, a user may also graphically visualize or apply the ischemia tool described herein. When selecting the ischemia detection tool, a user may interactively select the time point (e.g., J+80) or a time range over which to detect ischemia. For example, the user may select a point on an ECG waveform (e.g., a "virtual" or actual ECG waveform). The ECG analyzer may then calculate the NSTVM value. A visual signal corresponding to the detection of ischemia based on ST deviation may also be used, similar to the equipotential display, described above.

In one version, the user may select an "ischemia monitor" screen that displays one or more ECG signal waveforms (e.g., a simulated ECG waveform or actual ECG waveform) that are correlated with a 3D heart model. After selecting the time point from a signal waveform (e.g., selecting a point in the ST region of a waveform, such as the J+80 point), the ischemia monitor tool may display the isopotential graph (also referred to as a "stain") showing the location of the region of the heart that has a potential above the criterion threshold (e.g., 0.1 mV). The user may enter or modify the criterion threshold, or may select a suggested criterion. The criterion may be correlated to the normalization used on the ECG data; e.g., the heart vector may be normalized differently for different criterion.

The tool may also display a virtual signal waveform corresponding to the center of the "stain", either by a user moving the cursor along the surface of the heart until it is centered in the stain region, or automatically by the ECG analyzer.

Figure 15:
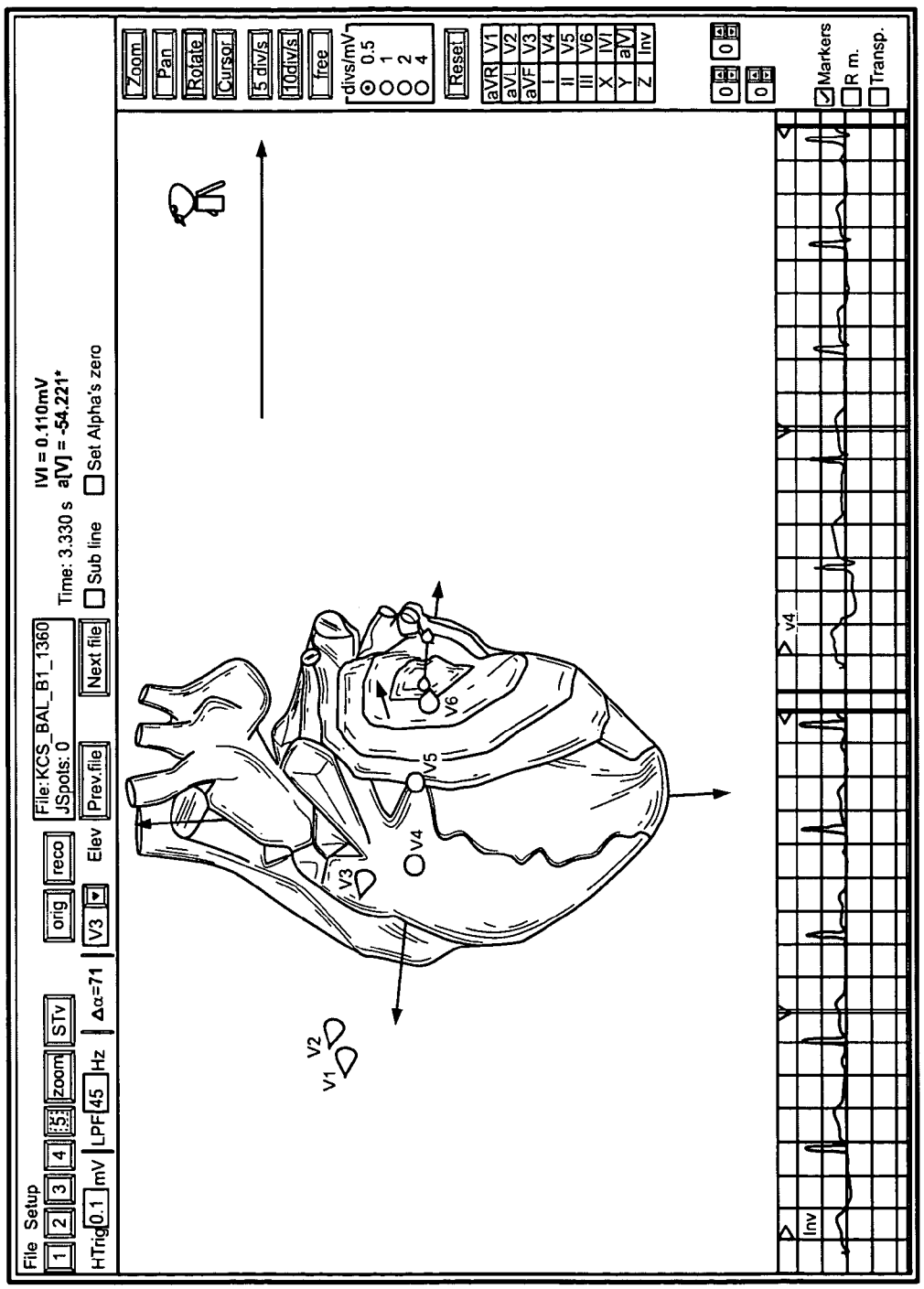
FIG. 15 shows an example of an ischemia tool using the ECG Analyzer as described herein.

FIG. 15 shows an example of the ischemia tool used with the ECG analyzer. The heart model 115 is shown indicating a stain pattern 120. The normalized heart vector is shown on the surface of the model heart as a white arrow 130. The "stains" on the model correspond to the signal level at the time point indicated by the vertical line 160, in either of the signal waveform windows 117, 115. The stain corresponds to ischemia level. The middle of the zone indicated on the heart model (indicated by the white arrow 130) is the point where the ST shift of the virtual ECG is largest.

EXAMPLE 3

Clinical Evaluation of Ischemia Detection

Preliminary clinical investigations have demonstrated that using the normalized ECG data as described herein may more reliably detect ST segment changes during myocardial ischemia, particularly in so-called "quiet zones" (e.g., regions of the heart where the standard ECG is relatively insensitive). A multi-center clinical study was initiated to investigate the diagnostic accuracy of the ECG analyzer described herein. Preliminary results compared the diagnosis of acute ischemia by evaluation of the ST segment using the standard 12-lead ECG and comparing it to the normalized ECG calculated as described herein.

This clinical trial was conducted in patients undergoing percutaneous transluminal coronary angioplasty (PTCA) in which the coronary artery was occluded with a PTCA balloon. Such patients serve as models for transient myocardial ischemia. Balloon occlusion assures complete obstruction of blood flow, and myocardium supplied by the artery will become ischemic within about 30 seconds to one minute. Thus, the study was designed to compare the ability of the ECG analyzer and standard ECG techniques to detect induced ischemia.

Methods. Standard ECGs were recorded from 51 patients undergoing PTCA. A total of 117 balloon occlusions were evaluated (46 occlusions in LADs, 34 in RCAs, 37 in LCx). The criteria for detecting ischemia on standard ECG were those set forth by the European Society of Cardiology/ American College of Cardiology Committee for the Redefinition of Myocardial Infarction. The criteria for determining ischemia using the normalized ECG data was an ST magnitude $\geq 0.1$ mv, measured 80 msec after the J point. ECGs were recorded using a custom-made digital ECG recorder and software, every 10 seconds with a 300-Hz sampling rate. For the ECG analyzer data, normalization was done using the six precoidial leads, as described herein. The ST segment shift was measured at the J+60 msec point. The last recording before the balloon deflation was analyzed as the most representative ECG recording for ischemia analysis Results. The ECG analyzer data showed substantially better sensitivity than the standard 12 lead ECG for detecting ischemia (90% versus 67%, respectively). Moreover, a sensitivity advantage for the ECG analyzer's normalized data was observed in each of the three coronary artery distributions. In each instance, the sensitivity advantage of the ECG analyzer over the standard ECG was statistically significant (Fisher's exact test; significance level $p \leq 0.05$, two sided alpha). When arterial distributions are compared, the ECG analyzer's advantage appeared greater in the RCA and LCx than in the LAD.

TABLE 1

Results of Ischemia Detection

| | | ECG Analyzer data | | | 12 lead ECG | | |
|---|---|---|---|---|---|---|---|
| Occlusion site | Number of occl. | posi- tive | nega- tive | sensi- tivity | posi- tive | nega- tive | sensi- tivity |
| LAD | 46 | 38 | 8 | 82.6% | 32 | 14 | 69.6% |
| RCA | 34 | 33 | 1 | 97.1% | 21 | 13 | 61.8% |

TABLE 1-continued

Results of Ischemia Detection

| Occlusion site | Number of occl. | ECG Analyzer data | | | 12 lead ECG | | |
|---|---|---|---|---|---|---|---|
| | | positive | negative | sensitivity | positive | negative | sensitivity |
| LCx | 37 | 34 | 3 | 91.9% | 25 | 12 | 67.6% |
| Total | 117 | 105 | 12 | 89.7% | 78 | 39 | 66.7% |

Conclusions. The ECG analyzer data that was normalized as described herein had an increased sensitivity for ischemia diagnoses of occlusions of different coronary arteries that is in good correlation with theoretical expectations. Even for occlusion sites that are theoretically well covered by precordial electrodes, the sensitivity difference between two methods is substantial (LAD, absolute 13% improvement in sensitivity), while for the sites out of precordial zone (RCA, absolute 35% increase and LCx, absolute 24% increase) the sensitivity difference is even more significant. Accordingly, the present clinical trial demonstrates that ECG analyzer has better sensitivity than the standard 12-lead ECG for detecting acute ischemia induced by arterial occlusion during PTCA.

The ischemia monitoring tool may be combined with other tools, or used in combination with other tools, including an ST Segment Elevation/Depression tool, which may provide localization information on ischemic events.

ST Segment Elevation/Depression Tool

The ECG analyzer may also provide information on the localization of electrical events on the heart model in cases where these events have a well defined location, such as the ischemic region (the source of the injury current of the ST segment), using an ST Segment Elevation/Depression tool that indicates the region of the heart giving rise to the electrical event. An ST Segment Elevation/Depression tool may compare a virtual ECG signal waveform with an actual ECG signal waveform (recorded at the same lead) to estimate the location of the heart region that gave rise to the potentially ischemic ST segment shift. An ST Segment Elevation/Depression may therefore enable both the localization of the ST segment shift, and identification of the type of the ST segment shift (e.g., elevation or depression).

Localization of a potentially ischemic ST segment shift, as well as the type of the ST segment shift (e.g., elevation or depression) may have significant diagnostic and therapeutic consequences. For example, ST segment depression in the anterior precordial leads may be due to an anterior subendocardial infarction, and ST segment elevation in the anterior precordial leads may be due to an anterior transmural infarction. However, ST segment depression or elevation may also be caused by subendocardial or transmural infarction located on the posterior wall of the heart. In such instances, an "opposite" effect may be seen. For example, ST segment elevation in chest leads may be due to a subendocardial infarction on the posterior region of the heart, whereas ST segment depression in chest leads maybe a transmural infarction on the posterior region of the heart. Furthermore, subendocardial infarctions and transmural infarctions may treated by completely different therapies, and there may be serious consequences if misdiagnosed.

The ST Segment Elevation/Depression tool exploits the difference between the "real" heart electrical activity and the approximation of the heart as a dipole. As previously described, electrical activity of the heart may be modeled as a dipole that is centered in the center of the heart. As a consequence of the dipole model, every cardiac electrical event simulated using the heart vector has a corresponding mirror image on the opposite side of the model heart that is of equal magnitude, but opposite in direction. Although a similar phenomena may be measured from actual electrodes on a patient (e.g., an electrical event recorded on one side of the body is "mirrored" on the opposite side of the body), differences arise because electrical activity typically originate from the walls of the heart, rather than the center of the heart. Thus, actual ECG waveforms will differ from "virtual" ECG waveforms (such as those calculated from a heart vector) in part, because of the "non-dipolar content" of the actual ECG waveforms. It is typical for a dipole approximation that the further from the electrical source (e.g., the heart) a recording is made, the more the source may appear to be a dipole. Thus, the closer a recording lead is to the heart, the larger the non-dipolar content of the recorded ECG. By comparing an actual ECG waveform recorded at a selected lead to a normalized virtual ECG waveform calculated using the heart vector for the same lead, it is possible to tell which "side" of the heart the electrical signal arose on, relative to the selected lead.

An ST Segment Elevation/Depression tool may be used after first identifying a potential ST segment shift. For example, when the NSTVM tool (or any Ischemia Monitoring tool) indicates that there is an ST segment shift greater than or equal to an ischemic criterion (e.g., 0.1 mV, 0.2 mV, etc) then the ST Segment Elevation/Depression tool may determine the region of the heart where the ST segment shift occurred. In some versions of the ST Segment Elevation/Depression tool, the tool first chooses an actual electrode which has the highest detectable ST segment shift. For example, the ST Segment Elevation/Depression tool may select the actual lead that is closest to the heart vector during the ST portion of an ECG waveform showing ST segment shift. Alternatively, the ST Segment Elevation/Depression tool may compare the ST portions of actual (or virtual) ECG waveforms for a plurality of leads and select the one having the greatest ST segment shift. The tool then calculates a virtual ECG waveform for this selected lead, either a normalized virtual ECG waveform (e.g., calculated with the normalized heart vector) or a non-normalized virtual ECG waveform (e.g., calculated with the non-normalized heart vector).

In some versions, the ST Segment Elevation/Depression tool then individually normalizes the virtual ECG waveform generated for the selected lead to the actual ECG waveform recorded at the selected lead. For example, the ECG waveform may be normalized by $\rho_i$ for the selected lead, where $\rho_i$ is calculated as previously described. Thus, the ECG waveform may be calculated from:

$$V_{Lead}(t) = \rho_i(l_x * X + l_y * Y + l_z * Z) \tag{20}$$

where $V_{Lead}(t)$ is the time-dependent voltage at the selected lead, $\rho_i$ is the lead normalization factor at the selected lead, $l_x$, $l_y$, and $l_z$ are the components of a lead vector at the selected lead, and X, Y, and Z are the orthogonal components of the heart vector. In some versions, the virtual ECG waveform may be normalized to the actual ECG waveform merely by normalizing the virtual ECG waveform to have the same peak value (e.g., the height of the R-wave). Thus, the virtual ECG waveform may be multiplied by the ratio of the peak R-waves from the actual and virtual ECG waveforms. This lead-specific normalization may help to accentuate the differences between the ST regions of the virtual and actual ECG waveforms at the selected lead.

The ST Segment Elevation/Depression tool may then compare the levels of the actual and virtual waveforms to determine how close the potentially ischemic ST segment shift was to the selected actual lead. Thus, if the absolute value of the ST region shift of the actual ECG waveform is larger than the absolute value of the ST segment shift of the normalized virtual ECG waveform, the signal may be on the same side of the heart as the selected actual lead. Likewise, if the absolute value of the ST region shift of the actual ECG waveform is smaller than the absolute value of the ST region shift of the normalized virtual ECG waveform, the signal may be on the opposite side of the heart from the selected actual lead. In some versions, the tool may also indicate a "confidence" level for this calculation. For example, the tool may further compare the differences between the normalized virtual ST region and the actual ST region (e.g., by subtracting the average values from these regions, or by comparing the means, medians, or other appropriate measures from these two regions), and offer a confidence value based on this difference. Thus, the tool may indicate a high confidence value, meaning that the tool is likely to have approximated the localization of the electrical event accurately, if the ST region of the normalized ECG waveform is more than 5%, 10%, 15% or 20% larger than the ST region of the actual ECG waveform.

Figure 16:
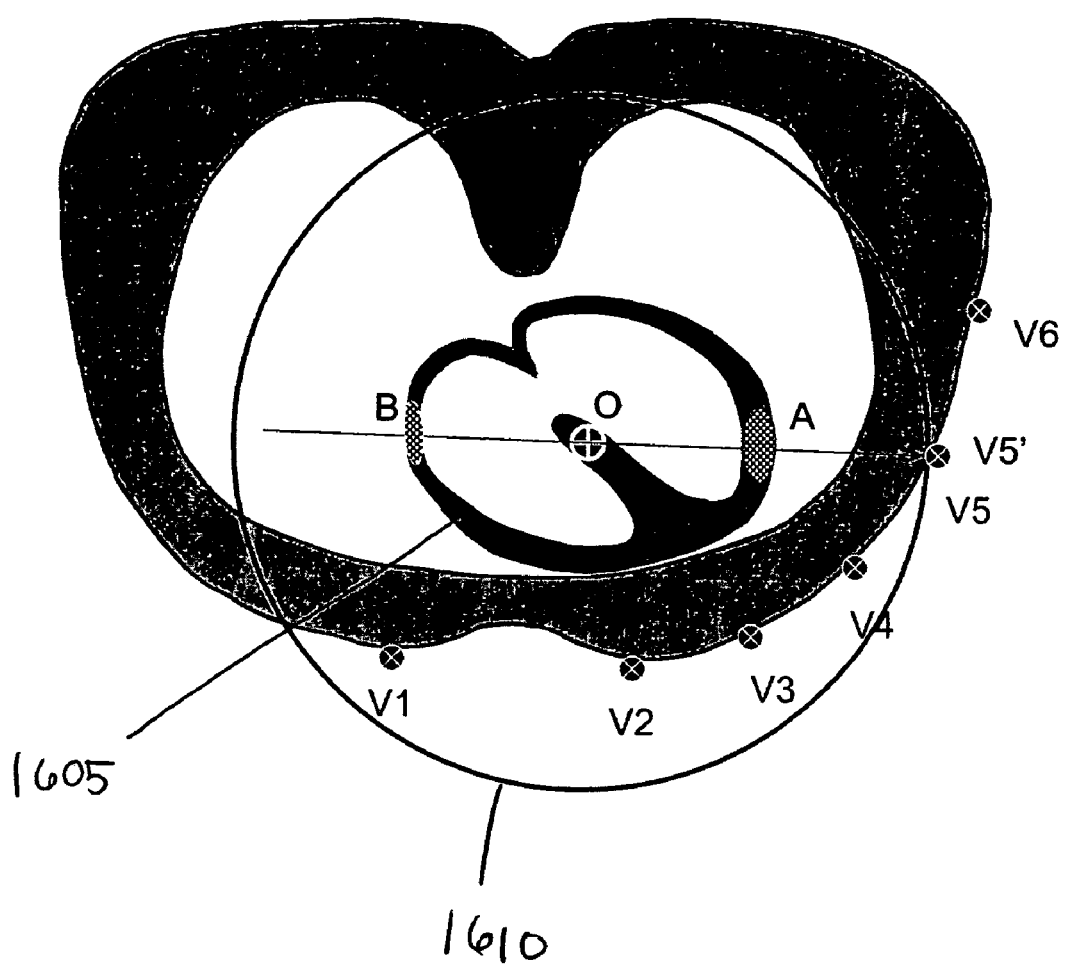
FIG. 16 shows an example of the ST Segment Elevation/Depression tool described herein.

FIG. 16 illustrates one example of the ST Segment Elevation/Depression tool. The signal level in an actual measuring electrode (e.g., V5) and a virtual measuring electrode (e.g., V5') may be compared to determine if the source of the signal (and therefore a potential ischemia) is closer to zone A (shown as the wall of the heart 1605) or is closer to more distant zone B, when compared to the heart center O. Note that in this particular example, the virtual waveform calculated at the virtual electrode V5' is normalized to the magnitude of the actual ECG waveform recorded at V5. This lead-specific normalization factor is shown as a virtual sphere 1610 (a circle in cross section) having a radius defined by lead normalization factor. This lead normalization factor may be different from the normalization factor ($\rho$) used to normalize the entire heart vector.

In addition to indicating the localization of ischemic infarction zones, the ST Segment Elevation/Depression tool may also indicate the type of ischemic event, such as transmural or subendocardial ischemia. For example, the tool may detect the type of ST segment shift (elevation or depression). In one version, the tool determines the type of ST segment shift by comparing the ST segment shift to a baseline level (e.g., from other portions of the waveform or from other waveforms).

An ST Segment Elevation/Depression tool may be used in conjunction with any other appropriate tool, particular an NSTVM tool or an Ischemia Monitoring tool, to characterize an ST segment shift. The tool may be applied automatically or selectively. Further, the tool may provide any appropriate output to indicate the result (including the confidence level of the result). For example, the ST Segment Elevation/Depression tool may alter an existing display (e.g., an equipotential plot showing a potential ischemic region) to indicate the localization of the ST level shift. Furthermore, the tool may indicate if the ST level shift is an elevation or a depression, and may further indicate if the ischemic event is transmural or subendocardial. In one version, the ST segment elevation/Depression tool indicates a likely localization of the ST elevation (e.g., to an anterior or posterior regions of the heart) by an indicative color. In one version, the tool may indicate localization or diagnosis as part of a text display.

Additional tools may also be used to indicate potential ischemia or other cardiac electrical events, including tools which analyze the angle of the heart vector or the direction of current flow through the heart.

Angle Analysis

The heart vector (including the normalized heart vector) may have a direction that is parallel to the direction of current across the heart. Thus, as current moves during cardiac electrical activity, the direction of the heart vector may reflect this movement. However, typical two-dimensional analysis of recorded ECG waveforms provides only a limited understanding of current flow across the heart. Thus, an analysis of the three-dimensional shape and motion of the heart vector may help interpret the electrical activity of the heart, and may provide new diagnostic tools and criterion. An Angle tool may be used to measure the angular difference in the heart vector over a selected time period.

Angle Tool (Heart Vector Spatial Angle Difference Tool)

The time varying heart vector reflects both the relative magnitude and the direction of the cardiac electrical activity of the heart. Thus, the direction of the heart vector changes over time, as may be seen from a heart vector hodograph, as previously described. An angle analysis tool, called an Angle tool, may be used to measure the difference in the angle between heart vectors in two or more time instants.

In general, the Angle tool compares the angle difference of two or more heart vectors. In one version, the user may interactively select two time points (e.g., from an ECG waveform) and the tool calculates the angular difference in the heart vector from those two time points. Interactive selection of the time points may be highly useful, because time points may be selected from displayed actual or virtual ECG waveforms. In some versions, automatic selection may be used (including waveform analysis to identify characteristic features). The tool may also analyze the heart vectors at the two specified times (or over the range of time). For example, the tool may calculate the variation in the angles of the heart vector over time, map the variation (e.g., differences) in the heart vector over this time. The tool may calculate any appropriate statistic, including but not limited to the rate of movement of the heart vector, the maximum and minimum differences in the heart vector, and the like. In some versions, the tool may display or otherwise provide statistical data. The tool may also display or provide graphical data. For example, the change in angle per unit time may be graphed and displayed, or the three-dimensional movement of the heart vector over the selected time range may be displayed, similar to the hodograph display previously described. As with all of the tools, data may be displayed, transmitted or stored.

In a Cartesian coordinate system, the angle between two heart vectors, A ($a_x$, $a_y$, $a_z$), and B ($b_x$, $b_y$, $b_z$), may be calculated from their orthogonal components ($a_x$, $a_y$, $a_z$ and $b_x$, $b_y$, $b_z$), from the following formula:

$$\cos(\alpha) = \frac{\vec{A} \cdot \vec{B}}{|\vec{A}| \cdot |\vec{B}|} = \frac{a_x b_x + a_y b_y + a_z b_z}{\sqrt{a_x^2 + a_y^2 + a_z^2} \sqrt{b_x^2 + b_y^2 + b_z^2}} \quad (21)$$

where $\alpha$ is the angle between the two heart vectors. The tool may determine the heart vectors A and B from specified time points (e.g., $t_0$ and $t_1$) using either a normalized or a non-normalized time dependent heart vector.

The tool may also be used automatically, in which pre-set times for measuring heart vector angles are specified. For example, a diagnostic criterion may be defined in which the difference in heart vectors over a known time period (e.g., J to J+80, etc.) is determined using the tool. Similarly, the tool may include criterion that can be applied to the spatial angular measurements derived by the tool. One example of such a criterion may be referred to as the ST-T angle.

The change in the spatial angle of the heart vector measured over the ST-T portion of the ECG waveform may be indicative of ischemia. For example, it has been proposed that, during ischemia, the current front moving in the heart over the ST to T portion of the heartbeat may change direction by a characteristic amount (Hurst J. W., Abnormalities of the S-T segment—Part 1., Clin. Cardiol. 20(6): δ 11-20, 1997). Thus, the tool may use an ST-T angle criterion (or a set of criterion) to detect ischemia based on the difference in spatial heart angle over the mid ST to T region of time. For example, the tool may indicate a likelihood of ischemia if it detect that the ST-T angle of the heart vector is above a criterion angle. The ST-T angle criterion may be set to more than about 80°, more than about 60°, more than about 40°, more than about 30°, more than about 20° or more than about 10° change in the spatial angle over this time period. Furthermore, the tool may be used to empirically determine (or evaluate) such a criterion. Thus, the tool may be used to precisely apply diagnostic criterion to a heart vector.

The Angle tool may also be used to investigate and apply new diagnostic criterion. For example a relative lack of change in the heart vector angle over the ST region of the heart vector may also be indicative of ischemia. Thus, the tool may determine if the heart vector over the ST region of the heart cycle has changed less than some criterion. This test may be referred to as the S-T Angle test. Time points spanning some portion (or all of) the ST region of the heart cycle may be selected either interactively, as described herein, or automatically (e.g., by selecting time points such as J, J+60, J+80, etc.). The tool may then determine how much the heart angle changes over the selected time period, and compare this to an S-T angle criterion. For example, the tool may indicate a likelihood of ischemia if it detects that the S-T angel of the heart is below a spatial S-T angle criterion. In one version, the S-T angle criterion may be less than about 10°. In one version, the S-T angle criterion may be less than about 20°. In one version, the S-T angle criterion may be less than about 30°. In one version, the S-T angle criterion may be less than about 40°. In one version, the S-T angle criterion may be less than about 50°. In one version, the S-T angle criterion may be less than about 60°. Thus, the tool may indicate when the S-T angle criterion has been exceeded, and/or may indicate a potential likelihood of ischemia based on the application of the S-T angle criterion. In some versions, a criterion such as the S-T angle criterion may be a set of values, or a look-up table, which gives a weighted probably of a cardiac event such as ischemia. In one example, the change in the angle over the ST portion of a set of waveforms was analyzed using data recorded from induced ischemia, as described in Example 3, above.

EXAMPLE 4

Application of the S-T Angle Criterion

The change in the angle during the ST region of the heart cycle was analyzed using an Angle tool. The tool provided the change in the angle (described in a range of ΔS-T angle criterion) over this time period. The ST period was selected using the tool off of representative ECG traces at the J and J+80 points. The change in the heart angle measured by the tool is shown in table 2:

TABLE 2

| S-T Angle ranges over the J and J + 80 range (out of 117 total PTCA procedures): | |
|---|---|
| ΔS-T angle (°) | No. of cases |
| <10 | 29 |
| <20 | 60 |
| <30 | 74 |
| >50 | 20 |

This preliminary study shows that the tool may be used to measure angles from the heart vector for selected time points (e.g., corresponding to the S-T region). Further, the tool may also apply a criterion or table of criterion (either pre-set or user selected) to measured data, and may display the measurement and the result in any appropriate manner. The tool may also be used to determine new criterion, or to test existing criterion.

Thus, the Angle tool may be valuable for increasing the specificity of diagnosis of phenomena such as ischemia. In particular, the tool may be combined with additional tools or tests and thereby help distinguish ischemic and non-ischemic events. For example, the Angle tool may measure and test the S-T angle, ST-T angle, or both, and may be used in conjunction with the NSTVM and/or Ischemia Monitoring tool. This not only adds an additional layer of detection, but may also help further diagnose the type of cardiac event and shore up failing of individual methods. For example, angle measurement tests such as the S-T angle and ST-T angle tests may increase specificity in ischemia detection by distinguishing acute ischemia from early repolarization, pericarditis, and the like.

Region Mapping Tool

The movement of the heart vector with respect to time may also contain information correlated to the electrical excitability of the heart. For example, it is less likely that the heart vector will dwell in regions of the heart which are less electrically active. Furthermore, electrical activity in certain regions of the heart may be correlated with normal or abnormal cardiac activity. Thus, the ECG analyzer may include a Region Mapping tool for examining the regions of the heart where the heart vector does (or does not) traverse during one or more cardiac PQRST cycle.

A Region Mapping tool may follow the positions of the heart vector over the surface of the heart model over time, and may display such regions. For example, the tool may indicate (e.g., by color intensity) regions where the heart vector spends the most or least amount of time. The tool may be interactive, allowing the user to select the time period (e.g., from the entire data time period), display type (e.g., display on the heart model), and analysis features (e.g., displaying regions where the heart vector did or did not travel, etc.).

A Region Mapping tool may also include pre-set, or user defined, regions (or "continents") indicate regions of interest on the heart surface, and calculate and display information regarding the heart vector with respect to such regions. Such regions of interest may correspond to maps of "normal" or typical electrical activity and/or maps that may be typical of abnormal cardiac electrical activity. Other regions of interest include patient-specific regions such as infarction scars, prior ischemic regions, or the like. These "continents" may be displayed onto the heart model as well.

The Region Mapping tool may also display and follow the pathway taken by the heart vector as well as the amount of time that the heart vector spends in or out of particular surface regions. Furthermore, the tool may calculate or determine any other relevant statistic based on the path of the heart vector and any identified or selected regions. For example, the tool may identify regions of the heart that may correlate to damaged tissue, e.g., regions of old infarction. The heart vector may also be analyzed (or "scored") based on dwell time of the heart vector in one or more heart surface regions. For example, "continents" may be defined for both a healthy heart axis (e.g., the heart vector in the QRS complex), and the deviated or infarction heart axis on the basis of the Q-wave. The Q-wave (which may be a sign of an infarction scar) is a deviation of the electrical heart axis. These "continents" may be differently defined for different patient populations according to factors such as height, weight, gender, torso shape (girth), and the like.

In addition to tools which may help analyze the cardiac electrical activity of ECG information, the ECG analyzer may also include tools that may improve the accuracy of analysis and display data, such as tools that correct the ECG analyzer based on an approximation of heart orientation.

Heart Orientation

The orientation of the heart within the chest cavity may vary between patients. For example, the heart in an adult with a low body fat may be oriented more vertically (e.g., so that the long axis of the heart lies more parallel with the long axis of the body) than a heart in an obese or heavier adult. Similarly, an infant heart may be oriented less vertically than an adult heart. Thus, the approximation of the heart model described herein may be corrected by using heart orientation information. Furthermore, a Heart Orientation tool may be incorporated in the ECG analyzer for estimating the heart orientation based on patient data. The Heart Orientation model may also correct for the orientation of the heart in any part of the ECG analyzer that is effected by the orientation of the heart, such as "continent" location (e.g., region mapping).

The Heart Orientation tool may estimate the heart orientation based on patient-specific data. For example, actual heart orientation may be estimated by any appropriate technique and entered as part of the patient data (e.g., along with patient ECG data). Thus, a practitioner may use any device capable of determining heart orientation (e.g., X-Ray, PET scanner, CAT scanner, echocardiogram, etc.) either separately or as part of the ECG measurement process. For example, patient data may include information about fiduciary markers indicating the position of the heart leads relative to the chest and/or heart. In some versions, the lead location may be provided to the Heart Orientation tool. Thus, the Heart Orientation tool may also correct for alignment of leads, particularly "standard" lead formations. Heart orientation may also be estimated by one trained or experienced in approximation of heart orientation, such as a nurse or technician. Heart orientation (including lead orientation) data may then be provided to the Heart Orientation tool.

In some versions, the Heart Orientation tool approximates heart orientation based on physical factors such as age, gender, body weight, torso circumference (girth), or the like. For example, a look-up table correlating any (or all) such factors may be provided to approximate heart orientation. Such a look-up table may be determined empirically or experimentally. Further, the heart orientation tool may be modified (e.g., by the addition of new data). In some versions, the heart orientation tool may be selectively applied to either the display or the data analysis, or both. In some versions, the user may compare data adjusted for heart orientation with unadjusted data.

A Heart Orientation tool may also adjust the orientation of the heart used in various aspects of the ECG analyzer described herein. For example, the Heart Orientation tool may correct the orientation of the model heart. Thus, the model heart may initially be oriented to some typical (or average) position, or a position based on other patient data, and the Heart Orientation tool may reoriented the heart model based on approximated heart orientation data. Thus, the display of the heart model showing one or more cardiac electrical signals (e.g., heart vector, hodographs, equipotential plots, etc.) may be adjusted using the heart orientation, potentially making the visual display and analysis of the heart more accurate. The location of the leads (e.g., the precordial leads) on the heart model may be adjusted based on the heart orientation. In some versions, the Heart Orientation tool may also correct the positional directions of a lead vector, L. The Heart Orientation tool may also be used in conjunction with any of the tools described herein.

Although the methods, articles of manufacture, systems, and devices described herein have discussed ischemia and methods of detecting ischemia, the invention should not be limited to ischemia, and should apply to the analysis, diagnosis or treatment of any cardiac electrical phenomena (e.g., abnormalities in cardiac electrical conduction processes, disturbances of heart rhythm or dysrhythmias, infarction, prolonged QT syndrome, etc.).

Further, although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Furthermore all references cited herein are intended to be fully incorporated herein in their entirety.

What is claimed is:

1. A method for analyzing cardiac electrical activity comprising:

obtaining ECG data measured from a plurality of actual lead sites on the surface of a patient's body;

computing from the ECG data measured at the plurality of actual lead sites, a time variable heart vector that represents size and orientation of a time varying electrical dipole that approximates electrical heart activity and that has an origin near the center of the patient's heart; and normalizing the time variable heart vector by a normalization factor without changing the direction of the time variable heart vector, wherein the normalization factor is computed from the patient's ECG data.

2. The method of claim 1, further comprising:
selecting a position corresponding to a virtual lead; and
producing information concerning electrical potential corresponding to the selected position by scalar multiplication of the produced normalized time variable heart vector and a lead vector that corresponds to the selected position.

3. The method of claim 1, wherein normalizing the time variable heart vector comprises normalizing the heart vector to a normalization surface having a selected attenuation value.

4. The method of claim 1, further comprising computing a normalization factor,
wherein computing a normalization factor comprises computing a lead normalization factor, $\rho_i$, for an actual lead site according to the ratio:

$$\rho_i = \frac{\int_0^T V_i(t) \cdot \left[\vec{H}(t) \cdot \vec{L}_i\right] dt}{\int_0^T \left[\vec{H}(t) \cdot \vec{L}_i\right]^2 dt}$$

wherein $V_i(t)$ is the measured voltage over time from an actual lead site, $\vec{H}(t)$ is the time variable heart vector, $\vec{L}_i$ is a lead vector corresponding to the actual lead site, and T is a time period.

5. The method of claim 4,
wherein computing a normalization factor comprises:
computing lead normalization factors from a plurality of actual lead sites; and
selecting a normalization factor from within the range defined by the maximum and the minimum lead normalization factors computed for the plurality of actual lead sites.

6. The method of claim 5, wherein selecting a normalization factor from within the range defined by the maximum and the minimum lead normalization factors computed for the plurality of actual lead sites includes selecting the average value of the plurality of lead normalization factors.

7. A method for visualizing cardiac electrical activity comprising:
obtaining ECG data measured from a plurality of actual lead sites on the surface of a patient's body;
computing from the ECG data measured at the plurality of actual lead sites, a time variable heart vector that represent size and orientation of a time varying electrical dipole that approximates electrical heart activity and that has an origin near the center of the patient's heart;
normalizing the time variable heart vector by a normalization factor, wherein the normalization factor is computed from the patient's ECG data;
deriving a cardiac electrical signal from the normalized time variable heart vector; and
displaying the cardiac electrical signal using a representation of a three dimensional image of a model heart.

8. A method of analyzing cardiac electrical activity comprising:
obtaining ECG data measured at a plurality of actual lead sites on the surface of a patient's body;
computing from the ECG data measured at the plurality of actual lead sites, a time variable heart vector that represents size and orientation of a time varying electrical dipole that approximates electrical heart activity and that has an origin near the center of the patient's heart;
computing a normalization factor from the ECG data measured at the plurality of actual lead sites; and
producing information concerning a normalized time variable heart vector by scaling the time variable heart vector by the normalization factor.

9. A method of displaying cardiac electrical activity comprising:
obtaining ECG data measured at a plurality of actual lead sites on the surface of a patient's body;
computing from the ECG data measured at the plurality of actual lead sites, a time variable heart vector that represents size and orientation of a time varying electrical dipole that approximates electrical heart activity and that has an origin near the center of the patient's heart;
computing a normalization factor from the ECG data measured at the plurality of actual lead sites;
computing a normalized time variable heart vector by scaling the time variable heart vector by the normalization factor;
producing a three dimensional heart representation on a display screen having the same origin as the time variable heart vector;
indicating on the display screen a designated position on the heart representation; and
producing information concerning electrical potential corresponding to the designated position by scalar multiplication of the normalized time variable heart vector and a lead vector that corresponds to the selected position.

* * * * *